US009446553B2

(12) United States Patent
Humphrey et al.

(10) Patent No.: US 9,446,553 B2
(45) Date of Patent: *Sep. 20, 2016

(54) PTFE LAYERS AND METHODS OF MANUFACTURING

(71) Applicant: TriVascular, Inc., Santa Rosa, CA (US)

(72) Inventors: Joseph W. Humphrey, Santa Rosa, CA (US); Jeffrey B. Skiba, Chandler, AZ (US)

(73) Assignee: TriVascular, Inc., Santa Rosa, CA (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/230,318

(22) Filed: Mar. 31, 2014

(65) Prior Publication Data

US 2014/0300033 A1   Oct. 9, 2014

Related U.S. Application Data

(63) Continuation of application No. 12/915,636, filed on Oct. 29, 2010, now Pat. No. 8,728,372, which is a continuation of application No. 12/250,946, filed on Oct. 14, 2008, now abandoned, which is a continuation of application No. 11/106,150, filed on Apr. 13, 2005, now abandoned.

(51) Int. Cl.
*B29C 47/94* (2006.01)
*B29C 55/08* (2006.01)
*B29C 55/02* (2006.01)
(Continued)

(52) U.S. Cl.
CPC .............. *B29C 55/02* (2013.01); *A61F 2/07* (2013.01); *A61L 27/16* (2013.01); *A61L 27/56* (2013.01); *B29C 47/94* (2013.01); *B29C 55/005* (2013.01); *B29C 55/08* (2013.01); *A61F 2/89* (2013.01); *A61F 2002/065* (2013.01); *A61F 2002/075* (2013.01); *A61F 2220/005* (2013.01); *A61F 2250/0003* (2013.01); *B29K 2027/18* (2013.01); *Y10T 428/139* (2015.01); *Y10T 428/1352* (2015.01); *Y10T 428/1376* (2015.01); *Y10T 428/1393* (2015.01); *Y10T 428/249981* (2015.04); *Y10T 428/3154* (2015.04)

(58) Field of Classification Search
None
See application file for complete search history.

(56) References Cited

U.S. PATENT DOCUMENTS 2,578,522 A  12/1951  Edgar et al.
2,685,707 A   8/1954  Llewellyn et al.
(Continued)

FOREIGN PATENT DOCUMENTS

EP  0 473 694 B1  3/1992
EP  0 473 727 B1  3/1992
(Continued)

OTHER PUBLICATIONS

Haimovitch, L. and Patterson, N., "Robust growth is forecast for endovascular repair of AAAs." The BBI Newsletter, vol. 26, No. 5, pp. 113-144, (May 2003).
(Continued)

*Primary Examiner* — Jeffrey Wollschlager
(74) *Attorney, Agent, or Firm* — Hoffmann & Baron, LLP

(57) ABSTRACT

Thin PTFE layers are described having little or no node and fibril microstructure and methods of manufacturing PTFE layers are disclosed that allow for controllable permeability and porosity of the layers. In some embodiments, the PTFE layers may act as a barrier layer in an endovascular graft or other medical device.

18 Claims, 10 Drawing Sheets

(51) Int. Cl.
*A61F 2/07* (2013.01)
*A61L 27/16* (2006.01)
*A61L 27/56* (2006.01)
*B29C 55/00* (2006.01)
A61F 2/06 (2013.01)
B29K 27/18 (2006.01)
A61F 2/89 (2013.01)

(56) References Cited

U.S. PATENT DOCUMENTS

| | | | |
|---|---|---|---|
| 3,315,020 A | 4/1967 | Gore | |
| 3,664,915 A | 5/1972 | Gore | |
| 3,813,461 A | 5/1974 | Murayama et al. | |
| 3,953,566 A | 4/1976 | Gore | |
| 3,953,566 A | 4/1976 | Justice et al. | |
| 3,962,153 A | 6/1976 | Gore | |
| 4,049,589 A | 9/1977 | Sakane | |
| 4,096,227 A | 6/1978 | Gore | |
| 4,110,392 A | 8/1978 | Yamazaki | |
| 4,153,661 A | 5/1979 | Ree et al. | |
| 4,187,390 A | 2/1980 | Gore | |
| 4,208,745 A | 6/1980 | Okita | |
| 4,229,838 A | 10/1980 | Mano | |
| 4,248,924 A | 2/1981 | Okita | |
| 4,385,093 A | 5/1983 | Hubis | |
| 4,459,252 A | 7/1984 | MacGregor | |
| 4,478,665 A | 10/1984 | Hubis | |
| 4,482,516 A | 11/1984 | Bowman et al. | |
| 4,598,011 A | 7/1986 | Bowman | |
| 4,743,480 A | 5/1988 | Campbell et al. | |
| 4,760,102 A | 7/1988 | Moriyama et al. | |
| 4,833,026 A | 5/1989 | Kausch | |
| 4,871,365 A | 10/1989 | Dumican | |
| 4,877,661 A | 10/1989 | House et al. | |
| 4,902,423 A | 2/1990 | Bacino | |
| 4,955,899 A | 9/1990 | Della Corna et al. | |
| 4,957,669 A | 9/1990 | Primm | |
| 4,985,296 A | 1/1991 | Mortimer, Jr. | |
| 5,071,609 A | 12/1991 | Tu et al. | |
| 5,094,895 A | 3/1992 | Branca et al. | |
| 5,096,473 A | 3/1992 | Sassa et al. | |
| 5,098,625 A | 3/1992 | Huang et al. | |
| 5,110,527 A | 5/1992 | Harada et al. | |
| 5,152,782 A | 10/1992 | Kowligi et al. | |
| 5,321,109 A | 6/1994 | Bosse et al. | |
| 5,374,473 A | 12/1994 | Knox et al. | |
| 5,433,909 A | 7/1995 | Martakos et al. | |
| 5,466,509 A | 11/1995 | Kowligi et al. | |
| 5,474,824 A | 12/1995 | Martakos et al. | |
| 5,476,589 A | 12/1995 | Bacino | |
| 5,505,887 A | 4/1996 | Zdrahala et al. | |
| 5,512,360 A | 4/1996 | King | |
| 5,529,820 A | 6/1996 | Nomi et al. | |
| 5,552,100 A | 9/1996 | Shannon et al. | |
| 5,560,986 A | 10/1996 | Mortimer, Jr. | |
| 5,580,618 A | 12/1996 | Okino et al. | |
| 5,607,478 A | 3/1997 | Lentz et al. | |
| 5,620,763 A | 4/1997 | House et al. | |
| 5,628,786 A | 5/1997 | Banas et al. | |
| 5,641,373 A | 6/1997 | Shannon et al. | |
| 5,645,915 A | 7/1997 | Kranzler et al. | |
| 5,658,960 A | 8/1997 | Dolan | |
| 5,700,285 A | 12/1997 | Myers et al. | |
| 5,708,044 A | 1/1998 | Branca | |
| 5,712,315 A | 1/1998 | Dolan | |
| 5,718,973 A | 2/1998 | Lewis et al. | |
| 5,735,892 A | 4/1998 | Myers et al. | |
| 5,747,128 A | 5/1998 | Campbell et al. | |
| 5,749,880 A | 5/1998 | Banas et al. | |
| 5,769,882 A | 6/1998 | Fogarty et al. | |
| 5,772,884 A | 6/1998 | Tanaka et al. | |
| 5,789,047 A | 8/1998 | Sasaki et al. | |
| 5,800,512 A | 9/1998 | Lentz et al. | |
| 5,810,710 A | 9/1998 | Burgos | |
| 5,814,405 A | 9/1998 | Branca et al. | |
| 5,840,775 A | 11/1998 | Howard, Jr. et al. | |
| 5,869,156 A | 2/1999 | Chung | |
| 5,888,605 A | 3/1999 | Hachisuka et al. | |
| 5,910,277 A | 6/1999 | Ishino et al. | |
| 5,925,075 A | 7/1999 | Myers et al. | |
| 5,939,198 A | 8/1999 | Howard, Jr. et al. | |
| 5,955,016 A | 9/1999 | Goldfarb | |
| 5,972,441 A | 10/1999 | Campbell et al. | |
| 5,976,192 A | 11/1999 | McIntyre et al. | |
| 5,976,650 A | 11/1999 | Campbell et al. | |
| 5,993,489 A | 11/1999 | Lewis et al. | |
| 6,027,779 A | 2/2000 | Campbell et al. | |
| 6,027,811 A | 2/2000 | Campbell et al. | |
| 6,036,724 A | 3/2000 | Lentz et al. | |
| 6,039,755 A | 3/2000 | Edwin et al. | |
| 6,075,180 A | 6/2000 | Sharber et al. | |
| 6,103,172 A | 8/2000 | Newman et al. | |
| 6,143,675 A | 11/2000 | McCollam et al. | |
| 6,174,473 B1 | 1/2001 | Levy et al. | |
| 6,201,543 B1 | 3/2001 | O'Donnell et al. | |
| 6,254,978 B1 | 7/2001 | Bahar et al. | |
| 6,270,707 B1 | 8/2001 | Hori et al. | |
| 6,319,279 B1 | 11/2001 | Shannon et al. | |
| 6,355,063 B1 | 3/2002 | Calcote | |
| 6,368,347 B1 | 4/2002 | Maini et al. | |
| 6,372,136 B1 | 4/2002 | Nakatsuka | |
| 6,416,537 B1 | 7/2002 | Martakos et al. | |
| 6,423,089 B1 | 7/2002 | Gingras et al. | |
| 6,428,571 B1 | 8/2002 | Lentz et al. | |
| 6,436,135 B1 | 8/2002 | Goldfarb | |
| 6,471,687 B2 | 10/2002 | Butler et al. | |
| 6,500,532 B1 | 12/2002 | Ruefer et al. | |
| 6,517,571 B1 | 2/2003 | Brauker et al. | |
| 6,524,334 B1 | 2/2003 | Thompson | |
| 6,530,765 B1 | 3/2003 | Zdrahala et al. | |
| 6,540,780 B1 | 4/2003 | Zilla et al. | |
| 6,541,589 B1 | 4/2003 | Baillie | |
| 6,547,815 B2 | 4/2003 | Myers | |
| 6,605,119 B1 | 8/2003 | Colone et al. | |
| 6,616,876 B1 | 9/2003 | Labrecque et al. | |
| 6,620,190 B1 | 9/2003 | Colone | |
| 6,702,971 B2 | 3/2004 | Huang et al. | |
| 6,716,239 B2 | 4/2004 | Sowinski et al. | |
| 6,719,783 B2 | 4/2004 | Lentz et al. | |
| 6,743,511 B2 | 6/2004 | Dittrich et al. | |
| 6,776,604 B1 | 8/2004 | Chobotov et al. | |
| 6,890,463 B2 | 5/2005 | Martakos et al. | |
| 6,923,927 B2 | 8/2005 | Martakos et al. | |
| 6,984,242 B2 | 1/2006 | Campbell et al. | |
| 7,806,922 B2 | 10/2010 | Henderson et al. | |
| 7,857,843 B2 | 12/2010 | Henderson | |
| 2002/0011684 A1 | 1/2002 | Bahar et al. | |
| 2002/0065552 A1 | 5/2002 | Jayaraman et al. | |
| 2002/0068968 A1 | 6/2002 | Hupp | |
| 2002/0076542 A1 | 6/2002 | Kramer et al. | |
| 2002/0082675 A1 | 6/2002 | Myers | |
| 2002/0111667 A1 | 8/2002 | Girton et al. | |
| 2002/0183716 A1 | 12/2002 | Herweck et al. | |
| 2002/0198588 A1 | 12/2002 | Armstrong et al. | |
| 2003/0004559 A1 | 1/2003 | Lentz et al. | |
| 2003/0006528 A1 | 1/2003 | Edwin et al. | |
| 2003/0009210 A1 | 1/2003 | Sowinski et al. | |
| 2003/0060871 A1 | 3/2003 | Hill et al. | |
| 2003/0062650 A1* | 4/2003 | Martakos | A61F 2/06 264/209.3 |
| 2003/0074016 A1 | 4/2003 | Campbell et al. | |
| 2003/0097174 A1 | 5/2003 | Henderson | |
| 2003/0143330 A1 | 7/2003 | Loomis et al. | |
| 2003/0199992 A1 | 10/2003 | Schmitt | |
| 2005/0238872 A1 | 10/2005 | Kennedy et al. | |
| 2006/0233991 A1* | 10/2006 | Humphrey | A61F 2/07 428/36.91 |

FOREIGN PATENT DOCUMENTS

| | | | |
|---|---|---|---|
| EP | 0 407 566 B1 | 11/1994 | |
| EP | 0 646 151 B1 | 4/1995 | |
| EP | 0 664 107 A1 | 7/1995 | |
| EP | 0 680 406 B1 | 11/1995 | |

(56) References Cited

FOREIGN PATENT DOCUMENTS

| | | |
|---|---|---|
| EP | 0 775 472 A2 | 5/1997 |
| EP | 0 821 648 B1 | 2/1998 |
| EP | 0 823 672 A1 | 11/1998 |
| EP | 0 877 582 B1 | 11/1998 |
| EP | 1 163 991 A2 | 12/2001 |
| JP | 49-42773 A | 4/1974 |
| JP | 54-02177 A | 4/1979 |
| JP | 07-082399 A | 3/1995 |
| JP | 2003-80590 A | 3/2003 |
| WO | 90/08801 A1 | 8/1990 |
| WO | 90/14055 A1 | 11/1990 |
| WO | 91/01210 A1 | 2/1991 |
| WO | 92/22604 A1 | 12/1992 |
| WO | 94/15781 A1 | 7/1994 |
| WO | 95/05277 A1 | 2/1995 |
| WO | 96/24308 A1 | 8/1996 |
| WO | 96/28115 A1 | 9/1996 |
| WO | 96/33066 A1 | 10/1996 |
| WO | 96/34911 A1 | 11/1996 |
| WO | 97/25938 A1 | 7/1997 |
| WO | 97/27820 A1 | 8/1997 |
| WO | 97/32714 A1 | 9/1997 |
| WO | 98/12989 A1 | 4/1998 |
| WO | 98/33453 A2 | 8/1998 |
| WO | 98/33638 A1 | 8/1998 |
| WO | 00/42947 A2 | 7/2000 |
| WO | 00/42948 A2 | 7/2000 |
| WO | 00/71179 A1 | 11/2000 |
| WO | 02/36332 A2 | 5/2002 |
| WO | 02/41804 A1 | 5/2002 |
| WO | 02/100454 A1 | 12/2002 |
| WO | 03/003946 A1 | 1/2003 |
| WO | 03/015666 A2 | 2/2003 |
| WO | 03/026713 A1 | 4/2003 |
| WO | 2004/004966 A1 | 1/2004 |

OTHER PUBLICATIONS

Uflacker, R. and Robison, J., "Endovascular treatment of abdominal aortic aneurysms: a review," Eur. Radial, 11:739-753 (2001).
Patent Abstract of JP 54-02177.
Machine Translation of JP 07-082399.
Machine Translation of JP 2003-80590.
Machine Translation of JP 49-42773.

* cited by examiner

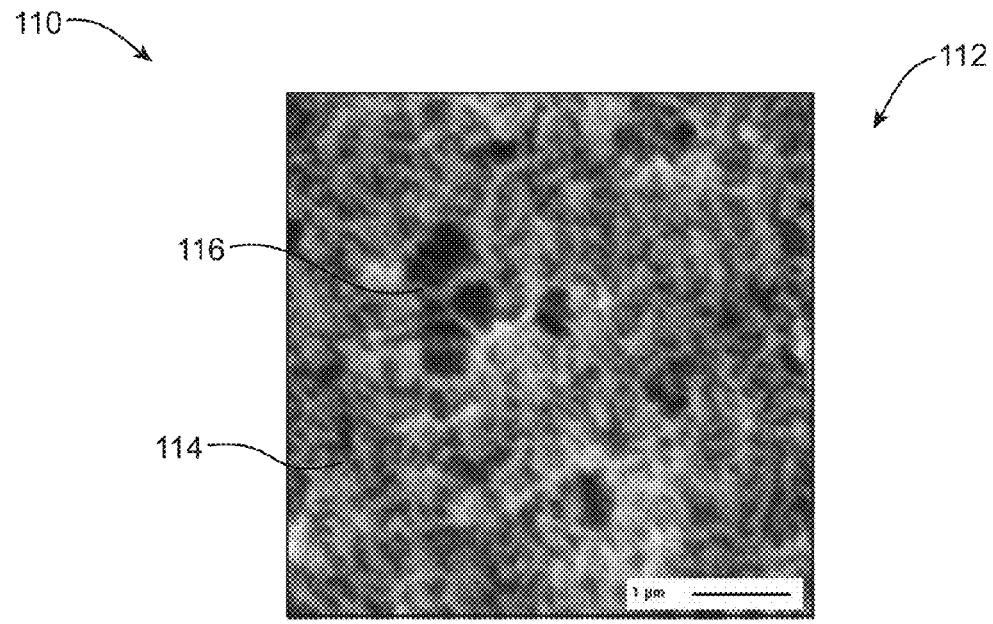
FIG. 9 (20,000x)
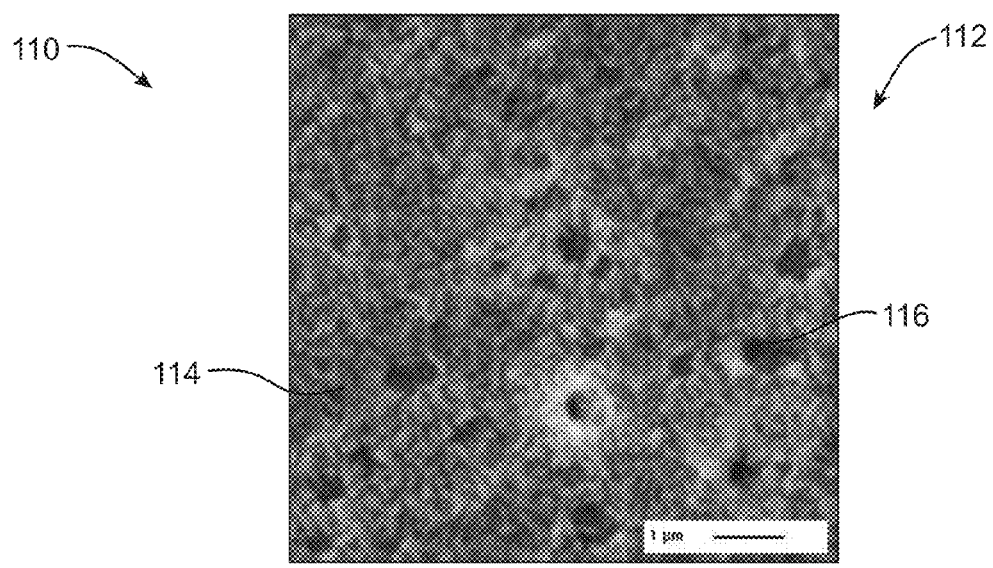
FIG. 10 (14,000x)

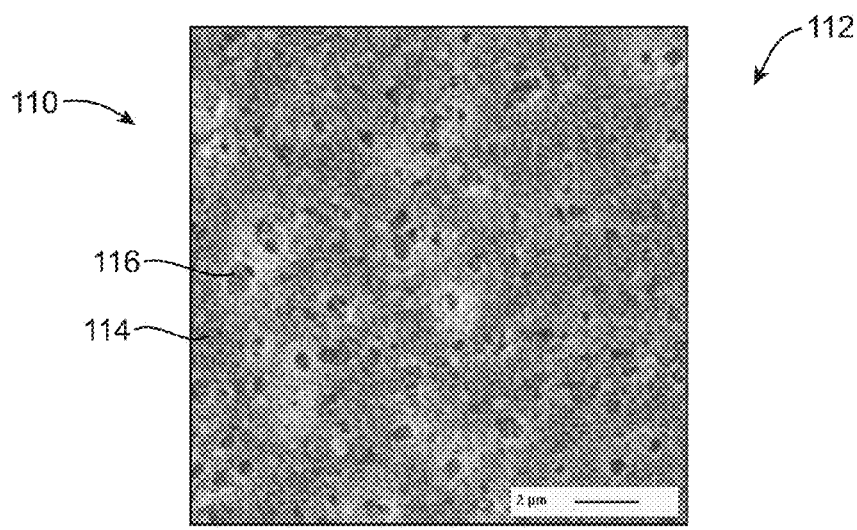
FIG. 11 (7,000x)
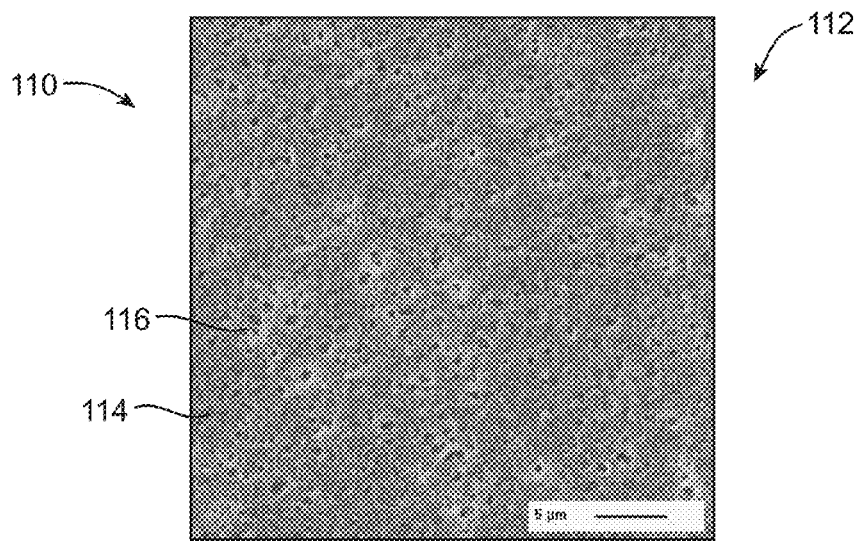
FIG. 12 (3,000x)

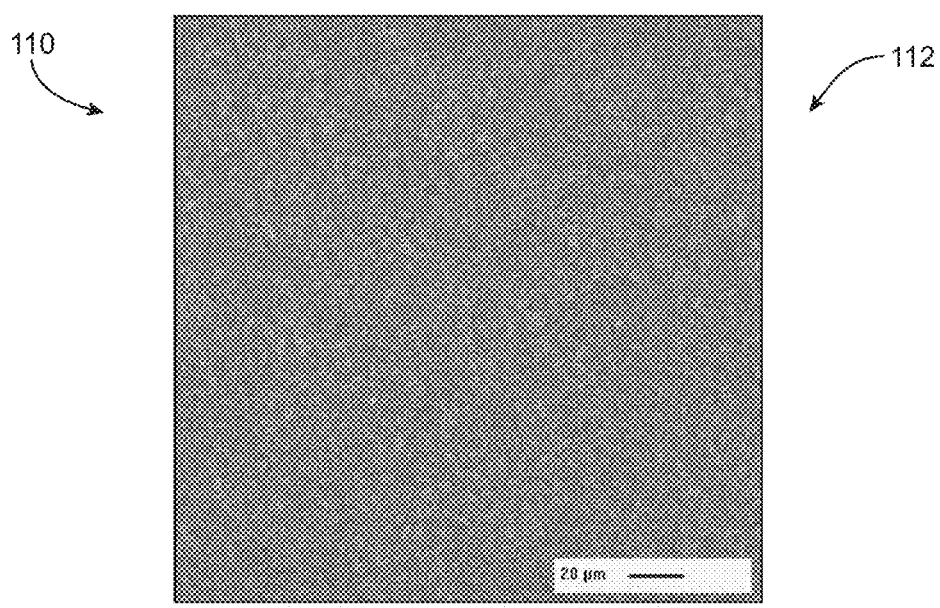
FIG. 13 (500x)

PTFE LAYERS AND METHODS OF MANUFACTURING

CROSS-REFERENCE TO RELATED APPLICATIONS

This application is a continuation of U.S. patent application Ser. No. 12/915,636, filed Oct. 29, 2010, which is a continuation of U.S. patent application Ser. No. 12/250,946, filed Oct. 14, 2008, abandoned, which is a continuation of U.S. patent application Ser. No. 11/106,150, filed Apr. 13, 2005, abandoned, the contents of which are incorporated herein by reference.

BACKGROUND OF THE INVENTION

Polytetrafluoroethylene (PTFE) layers have been used for the manufacture of various types of intracorporeal devices, such as vascular grafts. Such vascular grafts may be used to replace, reinforce, or bypass a diseased or injured body lumen. One conventional method of manufacturing "expanded" PTFE layers is described in U.S. Pat. No. 3,953,566 by Gore. In the methods described therein, a PTFE paste is formed by combining a PTFE resin and a lubricant. The PTFE paste may be extruded. After the lubricant is removed from the extruded paste, the PTFE article is stretched to create a porous, high strength PTFE article. The expanded PTFE layer is characterized by a porous, open microstructure that has nodes interconnected by fibrils.

Such an expansion process increases the volume of the PTFE layer by increasing the porosity, decreasing the density and increasing the internodal distance between adjacent nodes in the microstructure while not significantly affecting the thickness of the PTFE layer. As such, the conventional methods expand the PTFE layer and impart a porosity and permeability while only providing a negligible reduction in a thickness of the PTFE layer. In situations where a thin PTFE layer, and specifically, a thin PTFE layer having a low fluid permeability is needed, conventional PTFE layers are largely unsatisfactory due to the porosity and highly permeable nature of the expanded PTFE layer.

Therefore, what has been needed is improved PTFE layers and improved methods for manufacturing the PTFE layers. In particular, it would be desirable to have thin PTFE layers that have a controllable permeability to fluids (gases, liquids or both). It may also be desirable to have such thin PTFE layers that have a high degree of limpness and suppleness to allow mechanical manipulation or strain of such a PTFE layer without significant recoil or spring back.

BRIEF SUMMARY OF THE INVENTION

Embodiments of the present invention provide PTFE layers and films and methods of manufacturing the PTFE layers and films. Embodiments of the present invention may include one or more layers of a fluoropolymer, such as PTFE. Embodiments of PTFE layers may include at least a portion that does not have a significant or discernable node and fibril microstructure.

In one embodiment, a method of processing PTFE includes providing a layer of PTFE, applying stretching agent to at least a portion of the layer of PTFE and stretching the layer of PTFE while the layer of PTFE is wet with stretching agent. In another embodiment, a method of processing PTFE includes providing a layer of PTFE, applying stretching agent to at least a portion of the layer until a saturated portion of the surface is saturated with stretching agent and stretching the layer of PTFE while the layer of PTFE is saturated with stretching agent. In another embodiment, a method of processing PTFE includes providing a stretched layer of PTFE that has been stretched in at least a first direction, applying stretching agent to at least a portion of the stretched layer and stretching the stretched layer of PTFE while the layer of PTFE is wet with stretching agent. Also, for some embodiments, the direction of the first direction and the direction of the second stretch may be substantially the same or different. For example, in one embodiment, the first direction is the machine direction and the second stretch is carried out or performed in the transverse direction. In another embodiment, the first direction is the machine direction and the second stretch is carried out in substantially the same machine direction. In other embodiments, the first direction may be a transverse direction. Also, for some embodiments, the stretch in the first direction may have been carried out with sufficiently low stretching agent content so as to produce a significant or discernable node and fibril microstructure during the stretch in the first direction. In other embodiments, the stretch in the first direction may have been carried out while the layer of PTFE was wet with stretching agent to the extent that little or no node and fibril microstructure was created during the stretch in the first direction.

In another embodiment, a method of processing PTFE includes providing a layer of PTFE, applying stretching agent to at least a portion of the layer of PTFE, stretching the layer of PTFE while the layer of PTFE is wet with stretching agent, stretching the stretched layer of PTFE a second time and calendering the twice stretched layer of PTFE so as to densify, compress and further thin the material. Another embodiment is directed to a method of processing PTFE including providing a layer of PTFE, applying stretching agent to at least a portion of the layer until at least a portion of the layer is saturated with the stretching agent to form a saturated portion and stretching the layer of PTFE. Other embodiments include PTFE layers made by any combination of the methods discussed above.

Regarding layer embodiments, one layer embodiment is directed to a thin PTFE layer having low porosity, low fluid permeability, substantially no node and fibril structure, and having a thickness of about 0.00005 inch to about 0.005 inch. Another embodiment is directed to a thin PTFE layer, having substantially low porosity, substantially low fluid permeability, substantially no node and fibril structure, and a high degree of limpness and suppleness so to allow mechanical manipulation or strain of the PTFE layer without significant recoil or spring back.

In another embodiment, a PTFE composite film comprises a first layer including a stretched layer of PTFE that has a closed cell microstructure with a plurality of interconnected high density regions substantially free of node and fibril microstructure between the high density regions. The PTFE composite film also comprises a second layer of expanded PTFE which is secured to the first layer and which includes node and fibril microstructure. In another embodiment, a thin fluid-PTFE layer having low or substantially no fluid permeability is produced by providing a PTFE layer, adding a stretching agent to the PTFE layer and stretching the PTFE layer in at least one direction to reduce a thickness of the PTFE layer. In another embodiment, a thin layer of PTFE includes a stretched layer of PTFE that has a closed cell microstructure with a plurality of interconnected high density regions substantially free of node and fibril microstructure between the high density regions.

Another embodiment is directed to a multi-layered vascular graft that includes a first tubular body having an outer surface and an inner surface that defines an inner lumen of the vascular graft and a second tubular body having an outer surface and an inner surface coupled to the outer surface of the first tubular body. In this embodiment, one of the first tubular body and the second tubular body includes a fluid-permeable PTFE layer, and the other tubular body comprises a fluid-PTFE layer having low or substantially no fluid permeability. In another embodiment, an inflatable endovascular graft includes a body portion having an inflatable channel that defines an inflatable space. The inflatable space of this embodiment is at least partially surrounded by a thin PTFE layer having low or substantially no fluid permeability.

Another embodiment is directed to a stretched PTFE layer having low or substantially no fluid permeability that includes a closed cell microstructure having high density regions whose grain boundaries are directly interconnected to grain boundaries of adjacent high density regions and having substantially no node and fibril microstructure. In another embodiment, a composite film includes a fluid-permeable, expanded PTFE layer secured to a surface of a thin stretched PTFE layer having a closed cell microstructure, having high density regions whose grain boundaries are directly interconnected to grain boundaries of adjacent high density regions and having substantially no node and fibril microstructure.

Another embodiment is directed to a tubular structure having a composite film with a fluid-permeable, expanded PTFE layer secured to a surface of a thin, stretched PTFE layer. The thin, stretched PTFE layer has a closed cell microstructure with high density regions whose grain boundaries are directly interconnected to grain boundaries of adjacent high density regions and with substantially no node and fibril microstructure. In another embodiment, an endovascular graft includes a composite film with a fluid permeable, expanded PTFE layer secured to a surface of a thin stretched PTFE layer. The stretched PTFE layer has a closed cell microstructure with high density regions whose grain boundaries are directly interconnected to grain boundaries of adjacent high density regions and with substantially no node and fibril microstructure.

In another embodiment, a thin PTFE layer has substantially low porosity, low fluid permeability, substantially no node and fibril structure, and a high degree of limpness and suppleness so to allow mechanical manipulation or strain of the PTFE layer without significant recoil or spring back. In another embodiment, a thin layer of PTFE includes a stretched layer of PTFE that has a closed cell microstructure with a plurality of interconnected high density regions substantially free of node and fibril microstructure between the high density regions. In another embodiment, a method of controlling the porosity, density or both of a PTFE layer, includes stretching the PTFE layer at least one time at a preselected temperature and preselected stretching agent content for the at least one stretch.

These features of embodiments will become more apparent from the following detailed description when taken in conjunction with the accompanying exemplary drawings.

BRIEF DESCRIPTION OF THE DRAWINGS

FIG. 9 is a scanning electron microscope (SEM) image of a PTFE layer at a magnification of 20,000.

FIG. 10 is a SEM image of the PTFE layer of FIG. 9 at a magnification of 14,000.

FIG. 11 is a SEM image of the PTFE layer of FIG. 9 at a magnification of 7,000.

FIG. 12 is a SEM image of the PTFE layer of FIG. 9 at a magnification of 3,000.

FIG. 13 is a SEM image of the PTFE layer of FIG. 9 at a magnification of 500.

DETAILED DESCRIPTION OF THE INVENTION

Figure 1:
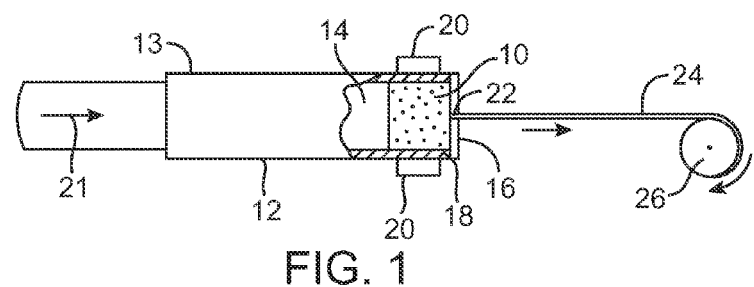
FIG. 1 illustrates a ram extruder extruding a PTFE ribbon that is being taken up on a spool.

Embodiments of the present invention relate generally to thin PTFE layers, PTFE films, composite films having two or more PTFE layers and methods of manufacturing the PTFE layers, films and composite films. Some particular embodiments are directed to thin PTFE layers having low or substantially no fluid permeability with a microstructure that does not include significant fibril and nodal structure as is common with expanded PTFE layers. It may also be desirable for some embodiments of such thin PTFE layers that have a high degree of limpness and suppleness so to allow mechanical manipulation or strain of such a PTFE layer without significant recoil or spring back. Such PTFE layers may be manufactured and used for construction of endovascular grafts or other medical devices. For some applications, embodiments of PTFE films may include one or more discrete layers of PTFE that are secured together to form a composite film. As used herein, the term "composite film" generally refers to a sheet of two or more PTFE layers that have surfaces in contact with each other, and in some embodiments, may be secured to each other such that the PTFE layers are not easily separated. The individual PTFE layers used in some of the PTFE composite film embodiments herein may have the thinness and low fluid permeability characteristics discussed above in combination with other layers having the same or different properties Some PTFE layer embodiments have a low fluid permeability while other PTFE layer embodiments have no or substantially no fluid permeability. A PTFE layer having a low fluid permeability may, for some embodiments, be distinguished from the permeability of a standard layer of expanded PTFE by comparing fluid permeability based on Gurley test results in the form of a Gurley Number or "Gurley Seconds". The Gurley Seconds is determined by measuring the time necessary for a given volume of air, typically, 25 cc, 100 cc or 300 cc, to flow through a standard 1 square inch of material or film under a standard pressure, such as 12.4 cm column of water. Such testing maybe carried out with a Gurley Densometer, made by Gurley Precision Instruments, Troy, N.Y. A standard porous fluid permeable layer of expanded PTFE may have a Gurley Number of less than about 15 seconds, specifically, less than about 10 seconds, where the volume of air used is about 100 cc. In contrast, embodiments of layers of PTFE discussed herein having low fluid permeability may have a Gurley Number of greater than about 1500 seconds where 100 cc of air is used in the test. An embodiment of a PTFE layer discussed herein having no or substantially no fluid permeability may have a Gurley Number of greater than about 12 hours, or up to a Gurley Number that is essentially infinite, or too high to measure, indicating no measurable fluid permeability. Some PTFE layer embodiments having substantially no fluid permeability may have a Gurley Number at 100 cc of air of greater than about $1 \times 10^6$ seconds. Stretched PTFE layers processed by embodiments of methods discussed herein having no discernable node or fibril microstructure may initially have substantially no fluid permeability. However, such PTFE layer embodiments may subsequently be stretched during a manufacturing process, such as the manufacture of an inflatable endovascular graft, during which process the PTFE layer may become more fluid permeable and achieve a level of low permeability as discussed above.

FIGS. 1-8 illustrate processing of PTFE material to form a thin, stretched PTFE layer having low or substantially no fluid permeability for particular fluids. As such, embodiments of the stretched PTFE layers are not "expanded" in the conventional sense as taught by Gore in, e.g., U.S. Pat. No. 3,953,566. For example, the stretched PTFE layers may be substantially thinned during stretching whereas prior art "expansion" processes typically leave the thickness of the expanded material somewhat unchanged but generate distinct nodal and fibril microstructure along with increased porosity and permeability in order to accommodate the expansion of the layer in plane of the layer.

Referring to FIG. 1, a fine PTFE resin powder is compounded with an extrusion agent such as a liquid lubricant to form a PTFE compound 10. A variety of different PTFE resins may be used such as the lower extrusion ratio, higher molecular weight fine powder coagulated dispersion resins (available from 3M Corporation, Ausimont Corporation, Daikin Corporation, DuPont and ICI Corporation) The PTFE molecules used in these resins typically have an average molecular weight of from about 20 million to about 50 million or more. Optionally, an additive, such as powdered or liquid color pigment or other resin additive may be added to the PTFE resin and lubricant to change the properties of the final PTFE layer. For example, a fluorinated copolymer may be added (such as perfluoropropylvinylether-modified PTFE) to improve the bondability of the PTFE layer. Additive is typically provided in a mass amount that is less than 2% of the mass of the PTFE resin, but it may be provided in any amount that produces a desired result. Additive may be combined with the PTFE resin before the lubricant is added so as to ensure homogenous mixing of the additive throughout the PTFE resin.

A variety of different types of extrusion and stretching agents, or lubricants, may be compounded with the PTFE powder resin. Some examples of lubricants that may be mixed with the PTFE resin include, but are not limited to, isoparaffin lubricants such as ISOPAR® H, ISOPAR® K and ISOPAR® M all of which are manufactured by ExxonMobil Corporation. Additional lubricants include mineral spirits, naphtha, MEK, toluene, alcohols such as isopropyl alcohol, and any other chemical that is capable of saturating the PTFE resin. In addition, two or more lubricants may be blended together for some lubricant embodiments. The amount of lubricant added to the PTFE resin may vary depending on the type of lubricant used as well as the desired properties of a final PTFE layer. Typically, however, the percent mass of lubricant for some compound embodiments may vary from about 15% to about 25% of the compound mass, specifically, from about 17% to about 22% of the compound mass, and more specifically from about 18% to about 20% of the compound mass.

The PTFE resin and lubricant may be mixed until a substantially homogenous PTFE compound 10 is formed. Compounding of the PTFE resin and lubricant is typically carried out at a temperature below the glass transition temperature of the PTFE resin which is typically from about 55° F. to about 76° F. Compounding of the PTFE resin may be carried out at a temperature below about 50° F., and specifically, at a temperature of from about 40° F. to about 50° F., so as to reduce shearing of the fine PTFE particles. Once mixed, the PTFE compound may be stored at a temperature of above approximately 100° F., and typically from about 110° F. to about 120° F. for a time period that ensures that the lubricant has absorbed through the PTFE resin particles. The storage time period typically may be greater than about six hours, and may vary depending on the resin and lubricant used.

Once the compounded PTFE resin and lubricant 10 have been suitably prepared, the compound 10 may be placed in an extruder, such as the ram extruder 12 shown in FIG. 1. The ram extruder 12 includes a barrel 13 and a piston 14 that is configured to slide within a chamber of the barrel 13 and form a seal against an inner cylindrical surface of the barrel 13. The compound 10 is placed in the chamber of the extruder 12 between the distal end of the piston 14 and an extruder die 16 sealed to the output end 18 of the extruder 12. The ram extruder 12 may also include heat elements 20 disposed about the output end 18 of the barrel 13 which are configured to uniformly heat the output end 18 of the extruder 12. In some methods, the output end 18 of the extruder is heated before the compounded PTFE resin 10 is loaded into the chamber. An embodiment of a ram extruder 12 may include a Phillips Scientific Corporation vertical three inch hydraulic ram extruder.

Once the PTFE resin compound is loaded, the piston 14 is advanced towards the output end 18 of the extruder 12, as indicated by arrow 21, which increases the chamber pressure and forces the PTFE compound 10 to be extruded through an orifice 22 of the die 16 to form an extrudate 24. The extrudate 24 may be in the form of a ribbon or tape that is then wound onto a take up spool 26 as indicated by the arrow adjacent the take up spool in FIG. 1. The ram extrusion process represents a mechanical working of the compound 10 and introduces shear forces and pressure on the compound 10. This working of the compound results in a more cohesive material in the form of extrudate ribbon or tape 24.

Processing conditions may be chosen to minimize the amount of lubricant that is evaporated from the PTFE extrudate ribbon 24. For example, the PTFE compound 10 may be extruded at a temperature that is above the glass transition temperature, and typically above about 90° F. The PTFE extrudate ribbon 24 is generally fully densified, non-porous and typically has approximately 100% of its original amount of lubricant remaining upon extrusion from the die 16. The die 16 may also be configured to produce an extrudate 24 having other configurations, such as a tubular configuration. Also, for some methods, the PTFE compound 10 may be processed to form a preform billet before it is placed in the extruder 12. In addition, a de-ionizing air curtain optionally may be used to reduce static electricity in the area of the extruder 12. In one example, the ram extruder 12 has a barrel 13 with a chamber having an inside transverse diameter of about 1 inch to about 6 inches in diameter. Embodiments of the die 16 may have orifices 22 configured to produce an extrudate ribbon or tape 24 having a width of about 1 inch to about 24 inches and a thickness of about 0.020 inch to about 0.040 inch, specifically, about 0.025 inch to about 0.035 inch.

Figure 2:
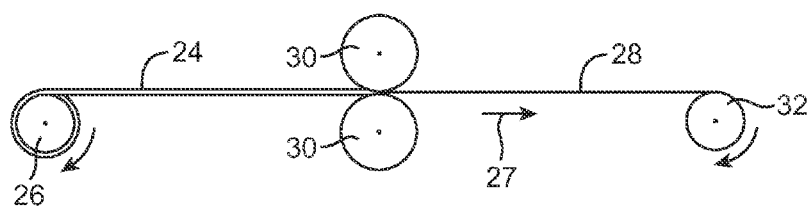
FIG. 2 illustrates a calendering process of the PTFE ribbon of FIG. 1.

After extrusion, the wet PTFE extrudate ribbon 24 may be calendered in a first direction or machine direction, as indicated by arrow 27, to reduce the thickness of the PTFE extrudate ribbon 24 into a PTFE layer 28 as shown in FIG. 2. During the calendering process, the width of the PTFE extrudate ribbon 24 and calendered PTFE layer 28 changes little while the PTFE extrudate ribbon 24 is lengthened in the machine direction. In one embodiment, the PTFE extrudate ribbon 24 and calendered PTFE layer 28 may be about 6 inches to about 10 inches in width. The calendering process both lengthens and reduces the thickness of the PTFE ribbon 24 to form PTFE layer 28 that is taken up by spool 32. During calendering, the PTFE extrudate ribbon 24 may be calendered between adjustable heated rollers 30 to mechanically compress and reduce the thickness of the PTFE ribbon 24. As such, the calendering process also encompasses a second mechanical working of the compound 10. Suitable equipment for the calendering process includes a custom 12 inch vertical calender machine manufactured by IMC Corporation, Birmingham, Ala.

While it may be possible to store the PTFE extrudate ribbon 24 for an extended period of time after extrusion, lubricant in the PTFE extrudate ribbon 24 will evaporate from the ribbon 24 during the storage period. As such, it may be desirable in some instances to calender the PTFE extrudate ribbon 24 almost immediately after extrusion so as to better control the lubricant level in the PTFE extrudate ribbon 24. For some embodiments, the PTFE ribbon 24 will have a lubricant content of about 15% to about 25% immediately prior to calendering.

Depending on the calendering speed and roller positioning, the PTFE ribbon 24 may be calendered down to produce a PTFE layer 28 of any suitable thickness. The reduction ratio of an embodiment of the calendering process, which is a ratio of the thickness of the PTFE extrudate ribbon 24 to the thickness of the calendered PTFE layer 28, maybe from about 3:1 to about 75:1, and specifically from about 7.5:1 to about 15:1. In one particular embodiment, for a PTFE extrudate ribbon 24 having a thickness of about 0.030 inch, calendering may reduce its thickness to about 0.001 inch to about 0.006 inch, specifically, from about 0.002 inch to about 0.004 inch. In some instances, the PTFE ribbon 24 may be calendered to a PTFE layer 28 which has a thickness that is slightly greater than a final desired thickness, so that the final stretch of the PTFE ribbon 24 causes the final PTFE layer 28 to have its desired thickness.

The calendering temperatures and processing parameters may be chosen so that the calendered PTFE layer 28 still has a significant amount of residual lubricant after the calendering process. For this embodiment, the adjustable rollers 30 may be heated to a temperature from about 100° F. to about 200° F., and specifically from about 120° F. to about 160° F. during the calendering process. After calendering, a residual amount of lubricant will remain in the PTFE layer 28 which typically may be from about 10% to about 22% lubricant by weight remaining, specifically about 15% to about 20% lubricant by weight.

Once the PTFE ribbon 24 has been calendered to produce PTFE layer 28, PTFE layer 28 then may be mechanically stretched transversely (also called the cross machine direction), in the longitudinal direction (also called the machine direction), in both of these directions or any other suitable direction or combination of directions, in order to thin the PTFE layer 28, generate a suitable microstructure and mechanically work the PTFE. It should be noted that although this specification describes a process whereby a PTFE layer is stretched transversely, then stretched longitudinally and then densified, the order these steps are performed in may be changed. For example, a PTFE layer may be first stretched longitudinally then stretched transversely. Such a layer optionally may then be densified as discussed below. For the transverse stretching process shown in FIGS. 3 and 4, a tentering machine 34 may be used to mechanically stretch the calendered PTFE layer 28 into a stretched PTFE layer 36. One embodiment of a suitable tentering machine 34 includes a 60 inch wide by 28 foot long tenter having a T-6 10 horsepower drive unit, manufactured by Gessner Industries, Concord, N.C.

Figure 3:
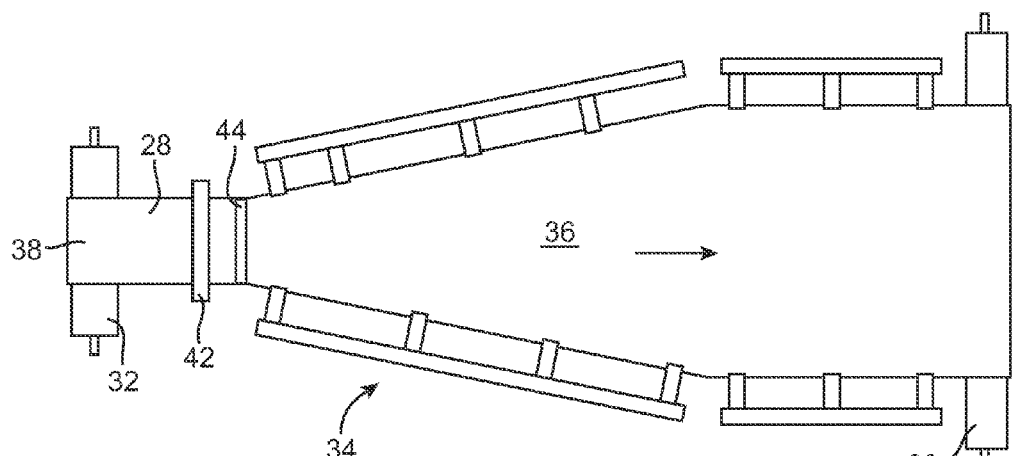
FIGS. 3 and 4 illustrate a tentering process with stretching agent being applied to a PTFE layer during the stretching process.
Figure 4:
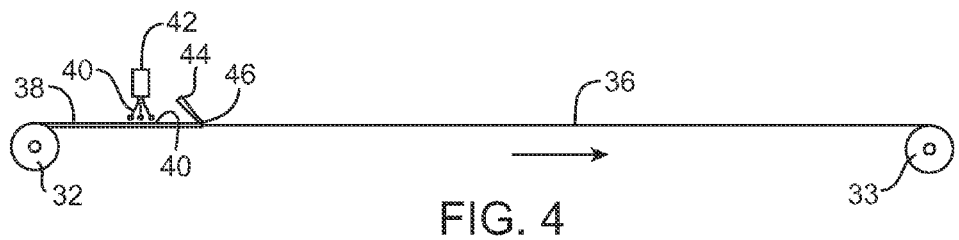

For some embodiments, in order to produce the desired combination of any of thickness, porosity, fluid permeability as well as mechanical properties, process parameters such as temperature, stretch ratios and material lubricant content of PTFE layer 28 may be controlled before and during the stretching process of the PTFE layer. As such, for some embodiments, a stretching agent or lubricant 40 optionally may be applied to the calendered PTFE layer 28 during the stretching process as shown in FIGS. 3 and 4. Applying the stretching agent 40 to the PTFE layer 28 prior to or during the stretching process of the PTFE layer 28 may be used to control the lubricant content of the stretched PTFE layer 36. This technique may be used to impart particular characteristics to the stretched PTFE layer 36 such as thinness, low porosity and low or substantially no fluid permeability. This method embodiment also allows for the stretched PTFE layer 36 to have a high degree of limpness and suppleness so to allow mechanical manipulation or strain of such a PTFE layer without significant recoil or spring back which may be particularly useful for some applications. If a high density, liquid-impermeable and gas-impermeable PTFE layer 28 having low or substantially no fluid permeability is desired, the PTFE layer 28 may be saturated throughout the thickness of the PTFE layer 28 with one or more stretching agents 40 during stretching. If a more porous PTFE layer 28 is desired, a lesser amount of stretching agent 40 will be applied onto the PTFE layer 28. Stretching the PTFE layer 28 may be carried out for some embodiments at a temperature of about 80° F. to about 100° F., specifically, about 85° F. to about 95° F.

The stretching agent 40 may be the same lubricant used to form the PTFE compound 10 or it may be a different lubricant or combination of lubricants. In some embodiments, the stretching agent may be applied in sufficient quantities to the PTFE layer 28 to saturate the PTFE layer 28 during the stretching process. The stretching agent maybe applied by a variety of methods to a surface, such as the upper surface 38, of the PTFE layer 28 during the stretching process. For example, the stretching agent 40 may be sprayed over the entire layer 28 or only on selected portions of the PTFE layer 28 by, e.g., a method such as by a spray mechanism 42 to the upper surface 38 of the PTFE layer 28. In such an embodiment, the stretching agent 40 is applied to the PTFE layer 28 after the PTFE layer 28 unwinds from spool 32 and passes under the spray mechanism 42. The stretching agent 40 may be applied uniformly over one or both sides of the PTFE layer 28, on only one side of the PTFE layer 28, or only on selected portions of the PTFE layer 28 at a temperature of typically about 70° F. to about 135° F., specifically, about 105° F. to about 125° F., and more specifically, about 110° F. to about 120° F.

If a PTFE layer having low or substantially no fluid permeability is desired, the PTFE layer 28 may be stretched in one or more directions while fully saturated until the desired thickness is achieved. It should be noted that as the PTFE layer 28 is stretched, the capacity of the resulting stretched PTFE layer 36 to absorb stretching agent 40 increases. As such, if it is desirable to maintain a saturated status of the PTFE layer 28 and stretched PTFE layer 36, it may be necessary to add stretching agent multiple times or over a large area in order to maintain that saturated state of the PTFE layer 36 and the effect of lubricant temperature for a period of time.

FIG. 4 illustrates the stretching agent or lubricant 40 being applied to upper surface 38 of the PTFE layer 28 by spray mechanism 42 as the PTFE layer 28 is being stretched transversely. For saturated stretching embodiments, it maybe necessary to apply sufficient stretching agent so as to pool or puddle the stretching agent on the upper surface 38 of the PTFE layer 28. The pooled or puddled stretching agent may be spread over the upper surface 38 of the PTFE layer 28 by a skimming member 44 that has a smooth contact edge 46 adjacent the upper surface 38 of the PTFE layer 28. While not shown, multiple skimming members may be used with some or all having a smooth contact edge or alternatively a grooved/patterned contact edge. The skimming member 44 is disposed adjacent the spray mechanism 42 displaced from the spray mechanism in the machine direction of the PTFE layer 28 such that the stretching agent 40 applied by the spray mechanism 42 runs into the skimming member 44 and is spread by the motion of the stretching agent 40 and PTFE layer 28 relative to the skimming member 44. The skimming member 44 may be in contact with the upper surface 38 of the PTFE layer 28 or also may be disposed slightly above the upper surface 38, depending on the desired configuration of the set up, the type of stretching agent being used as well as other factors.

Embodiments of methods discussed herein may be useful to reduce a thickness of the PTFE layer 28 to a stretched PTFE layer 36 of any thickness down to about 0.00005 inch; typically from about 0.00005 inch and 0.005 inch. Typical transverse stretch ratios may be from about 3:1 to about 20:1. In one embodiment, a calendered PTFE layer 28 having a width of about 3 inches to about 6 inches, may be transversely stretched, as shown in FIGS. 3 and 4, into a stretched PTFE layer 36 having a width of about 20 inches to about 60 inches. This represents a stretch ratio of about 3:1 to about 12:1. In another embodiment, a calendered PTFE layer 28 having a width of about 3.5 inches to about 4.5 inches may be transversely stretched, as shown in FIGS. 3 and 4, into a stretched PTFE layer 36 having a width of about 20 inches to about 60 inches. This represents a stretch ratio of about 7.8:1 to about 13:1.

As discussed above, the thickness, fluid permeability, porosity and average pore size of the PTFE layers 36 may be effected by the amount and temperature of stretching agent 40 applied to the layer 36 prior to or during stretching, the temperature of the layer, the stretching agent that is applied to the PTFE layer, or both, prior to stretching and the stretch rate. By adjusting these parameters, these characteristics may be optimized in order to produce a PTFE layer that is suited to a particular application. For example, if the PTFE layer 36 is used as a moisture barrier for clothing, the parameters may be adjusted to produce an average pore size of less than about 6 microns. Alternatively, if the PTFE layer 36 is used in an endovascular graft that benefits from tissue in-growth, the average pore size is adjusted to be greater than 6.0 microns. In other embodiments, where the PTFE layer 36 is a barrier layer for use in an endovascular graft, the pore size may be smaller, such as from about 0.01 micron to about 5.0 microns. In addition, embodiments of the stretched PTFE layer 36 are fusible and deformable and easily may be fused with or secured to other PTFE layers having different properties. At any point after the PTFE layer 28 is stretched, the stretched PTFE layer 36 may be sintered to amorphously lock the microstructure of the PTFE layer 36. Sintering may be performed to combine the stretched PTFE layer 36 with other layers of PTFE to form multi-layer composite films, such as those used for endovascular grafts and the like discussed below.

The stretched PTFE layer optionally may be subjected to a second stretching process, as shown in FIGS. 3, 4, 5 and 6, wherein the stretched PTFE layer 36 is formed into a twice-stretched PTFE layer 46. Once again, as discussed above, it is important to note that although the method embodiments discussed herein are directed to a first transverse stretch and subsequently to a longitudinal or machine direction stretch, the order of the stretch directions may be reversed and other combinations of stretch directions and numbers are also contemplated. For example, PTFE layer 28 may be stretched twice in the machine or longitudinal direction without any transverse stretching. PTFE layer 28 may be stretched first in a longitudinal or machine direction and then in a transverse direction. In addition, a PTFE layer 28 may be stretched three or more times. Some or all of the speeds, stretch ratios, temperatures, lubricant parameters and the like discussed herein may be the same but need not necessarily and typically will not be the same for any of these various stretching steps regardless of the order the stretching steps.

Figure 5:
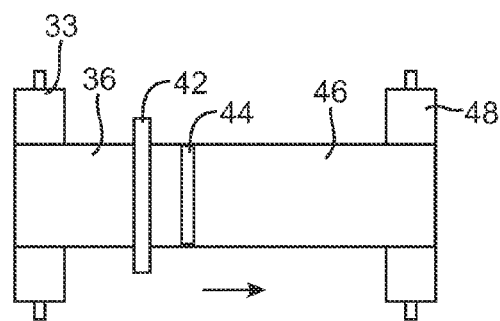
FIGS. 5 and 6 illustrate a machine direction stretching process of the stretched PTFE layer of FIGS. 3 and 4.
Figure 6:
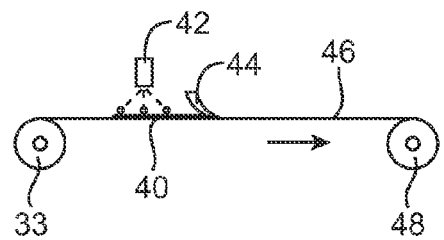
Figure 7:
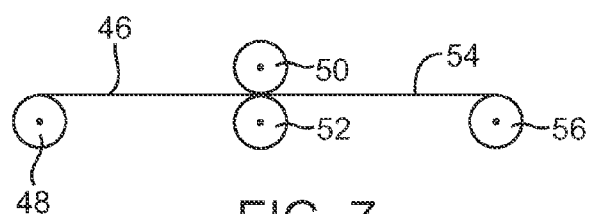
FIGS. 7 and 8 illustrate a final calendering or densification process performed on a stretched PTFE layer.
Figure 8:
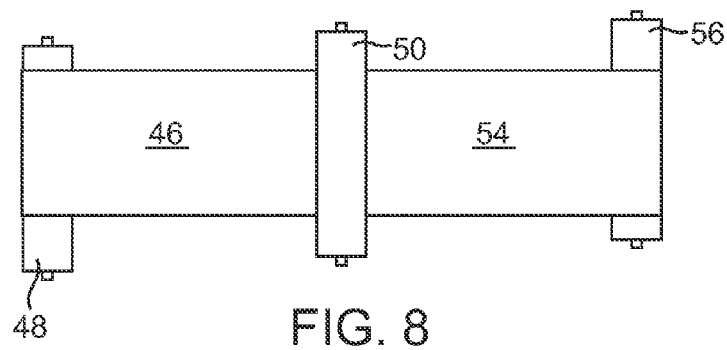

This optional second stretching process subjects the PTFE layer 36 to yet another mechanical working. The second stretching process shown in FIGS. 5 and 6 is being carried out in the machine direction; however, the second stretching process may also be carried out in any other suitable direction, such as transversely. The twice-stretched PTFE layer 46 is wound onto spool 48 after undergoing the second stretching process. Additional stretching agent 40 optionally may be applied to a surface of the stretched PTFE layer 36 as the layer 36 is being stretched a second time. If higher porosity and fluid permeability are desired, the second stretch may be performed with the stretched layer 36 in a dry state without the addition of lubricant during the second stretch. If the stretched PTFE layer 36 has residual lubricant without additional lubricant added, the second stretching process will generate a microstructure having significant nodes connected by fibrils. The second stretching process may be carried out at a temperature of about 85° F. to about 95° F. for some embodiments. The stretch ratio for the second stretch maybe up to about 20:1, specifically, about 6:1 to about 10:1.

If the PTFE layer 28 is stretched in two or more directions, the rate of stretching in the two directions; e.g., the machine direction and the off-axis or transverse direction, may have different or the same stretch rates. For example, when the PTFE layer 28 is being stretched in the machine direction (e.g., first direction), the rate of stretching is typically in the range from about two percent to about 100 percent per second; specifically, from about four percent to about 20 percent per second, and more specifically about five percent to about ten percent per second. In contrast, when stretching in the cross machine or transverse direction, the rate of stretching may be in the range from about one percent to about 300 percent per second, specifically from about ten percent to about 100 percent per second, and more specifically about 15 percent to about 25 percent per second.

Stretching in the different directions may be carried out at the same temperatures or at different temperatures. For example, stretching in the machine direction is generally carried out at a temperature below about 572° F., and for some embodiments, below about 239° F. In contrast, stretching in the transverse direction is typically carried out at a temperature above the glass transition temperature, and usually from about 80° F. to about 100° F. Stretching PTFE layers 28 at lower temperatures will reduce stretching agent 40 evaporation and retain the stretching agent 40 in the PTFE layer 28 for a longer period of time during processing.

Either the stretched PTFE layer 36 or the twice-stretched PTFE layer 46 optionally may be calendered in order to further thin and densify the material. The twice-stretched PTFE layer 46 is shown being calendered in FIGS. 7 and 8. In this example, the twice-stretched PTFE layer 46 is unwound from spool 48, passed through calender rollers 50 and 52, formed into a densified layer 54, then taken up on spool 54. The calender machine may be the same machine or a different machine as that indicated in FIG. 2 and discussed above. This final calendering or densification of PTFE layer 46 generally produces a highly densified PTFE layer 54 that has no discernable microstructure features, such as pores, and has low or substantially no fluid permeability. The methods of compressing and stretching PTFE layers may both be used to control thinning of the PTFE layer and the microstructure that results from the thinning process. The densified PTFE layer 54 may also lack the suppleness and limpness mechanical properties of the stretched PTFE layers 36 and 46 discussed above. The rollers 50 and 52 may be adjusted to have any suitable separation to produce a PTFE layer 54 having a thickness of about 0.00005 inch to about 0.005 inch. The rollers 50 and 52 may also be heated during the calendering process, with typical temperatures being from about 90° F. to about 250° F.; specifically, from about 120° F. to about 160° F.; more specifically, from about 130° F. to about 150° F.

The following example describes specific methods of manufacturing of the stretched PTFE layers 36. In this embodiment, 1000 grams of resin are compounded with an isoparaffin based lubricant; specifically, ISOPAR® M, in a mass ratio of lubricant-to-PTFE compound from about 15% to about 25%. Compounding of the PTFE resin and lubricant is carried out at a temperature below 50° F., which is well below the glass transition temperature of the PTFE resin of between about 57° F. to about 75° F.

The PTFE compound 10 maybe formed into a billet and stored at a temperature of about 105° F. to about 125° F. for six or more hours to ensure that the lubricant substantially has penetrated and absorbed through the resin. Thereafter, the PTFE compound 10 is placed in an extruder 12, as shown in FIG. 1. The PTFE compound 10 may then be paste extruded from the orifice 22 of the die 16 of the extruder 12 at a temperature above the resin glass transition temperature. In one embodiment, the paste is extruded at a temperature from about 80° F. to 120° F. A reduction ratio, e.g., a ratio of a cross sectional area of the PTFE compound 10 before extrusion to the cross section area of the PTFE extrudate 24 after extrusion, may be from about 10:1 to about 400:1, and specifically may be from about 80:1 to about 120:1. The extruder 12 maybe a horizontal extruder or a vertical extruder. The orifice 22 of the extrusion die 16 determines the final cross sectional configuration of the extruded PTFE ribbon 24. The orifice 22 shape or configuration of the extrusion die 16 may be tubular, square, rectangular or any other suitable profile. It may be desirable to preform the PTFE compound (resin and lubricant) into a billet.

The PTFE extrudate ribbon 24 is then calendered, as shown in FIG. 2, at a temperature from about 100° F. to about 160° F. to reduce a thickness of the PTFE ribbon 24 and form a PTFE layer or film 28. The temperature at calendering may be controlled by controlling the temperature of the rollers 30 of the calender machine. The PTFE layer may be calendered down to a thickness from about 0.001 inch to about 0.006 inch, and specifically, down to a thickness of about 0.002 inch to about 0.003 inch. At the end of the calendering, the calendered PTFE layer 28 may have a lubricant content of about 10% by weight to about 20% by weight.

Referring again to FIGS. 3 and 4, after calendering, one side or both sides of the calendered PTFE layer 28 are sprayed with an isoparaffin-based stretching agent 40 at a prescribed temperature so that the PTFE film or layer 28 is flooded and fully saturated through the thickness of the PTFE layer 28. The saturated, calendered PTFE layer may then be stretched in a direction that is substantially orthogonal to the calendering direction by a tentering machine 34 to reduce a thickness of the PTFE layer 28 and form a stretched PTFE layer 36. The stretched PTFE layer 36 may have a thickness of about 0.00005 inch to about 0.005 inch; specifically, the stretched PTFE layer 36 may have a thickness of about 0.0002 inch to about 0.002 inch. The PTFE layer 28 typically is tentered or stretched at an elevated temperature above the glass transition temperature, specifically, from about 80° F. to about 100° F., more specifically, about 85° F. to about 95° F.

Wet tentering with the stretching agent 40 allows the PTFE layer 28 to be thinned without creating substantial porosity and fluid permeability in the stretched PTFE layer 36. While the stretched PTFE layer 36 will have a porosity, its porosity and pore size typically will not be large enough to be permeable to liquids, and often will be small enough to have substantially no fluid permeability. In addition, the stretched PTFE layer embodiment 36 does not have the conventional node and fibril microstructure but instead has a closed cell microstructure in which boundaries of adjacent nodes are directly connected with each other. The fluid-impermeable stretched PTFE film or layer 36 typically may have a density from about 0.5 g/cm$^3$ to about 1.5 g/cm$^3$, but it may have a larger or smaller density for some embodiments. In addition, with regard to all of the methods of processing layers of PTFE discussed above, any of the PTFE layers produced by these methods may also be sintered at any point in the above processes in order to substantially fix the microstructure of the PTFE layer. A typical sintering process may be to expose the PTFE layer to a temperature of about 350° C. to about 380° C. for several minutes; specifically, about 2 minutes to about 5 minutes.

The various methods discussed above may be used to produce PTFE layers having a variety of desirable properties. The scanning electron microscope (SEM) images shown in FIGS. 9 to 13 illustrate different magnifications of a microstructure of a PTFE film or layer 110 made in accordance with embodiments of the present invention. PTFE layer 110 has a generally closed cell microstructure 112 that is substantially free of the conventional node and fibril microstructure commonly seen in expanded PTFE layers. Embodiments of the PTFE film 110 may have low fluid-permeability, or no or substantially no fluid-permeability. One or more of PTFE layer 110 may be used as a barrier layer to prevent a fluid such as a liquid or gas from permeating or escaping therethrough.

At a magnification of 20,000, as seen in FIG. 9, the microstructure of the stretched PTFE layer 110 resembles a pocked-like structure that comprises interconnected high density regions 114 and pockets or pores 116 between some of the high density regions 114. The PTFE film 110 may be considered to have a closed cell network structure with interconnected strands connecting high density regions 114 in which a high density region grain boundary is directly connected to a grain boundary of an adjacent high density region. Unlike conventional expanded PTFE ("ePTFE") which typically has a substantial node and fibril microstructure that is discernable when viewed at a SEM magnification of 20,000, PTFE layer 110 lacks the distinct, parallel fibrils that interconnect adjacent nodes of ePTFE and has no discernable node and fibril microstructure when viewed at a SEM magnification of 20,000, as shown in FIG. 9. The closed cell microstructure of the PTFE layer 110 provides a layer having low or substantially no fluid permeability that may be used as "a barrier layer" to prevent liquid from passing from one side of the PTFE layer to the opposite side.

Though PTFE film or layer 110 is configured to have low or substantially no fluid permeability, PTFE layer 110 nonetheless has a porosity. The PTFE layer 110 typically has an average porosity from about 20% to about 80%, and specifically from about 30% and about 70%. In one embodiment, a PTFE film 110 has a porosity of about 30% to about 40%. In another embodiment, a PTFE layer 110 has a porosity of about 60% to about 70%. Porosity as described in these figures is meant to indicate the volume of solid PTFE material as a percentage of the total volume of the PTFE film 110. An average pore size in the PTFE layer 110 is may be less than about 20 microns, and specifically less than about 0.5 micron. In one embodiment, a PTFE layer 110 has an average pore size of from about 0.01 micron to about 0.5 micron. As can be appreciated, if tissue ingrowth is desired, the PTFE film 110 may have an average pore size of greater than about 6.0 microns. As described below, depending on the desired properties of the resultant PTFE layer 110, embodiments of methods may be modified so as to vary the average porosity and average pore size of the PTFE film 110 in a continuum from 10 microns to 50 microns down to substantially less than about 0.1 micron.

PTFE layer 110 may have a density from about 0.5 g/cm³ to about 1.5 g/cm³, and specifically from about g/cm³ to about 1.5 g/cm³. While the density of the PTFE film 110 is typically less than a density for a fully densified PTFE layer (e.g., 2.1 g/cm³), if desired, the density of the PTFE layer 110 may be densified to a higher density level so that the density of the PTFE layer 110 is comparable to a fully densified PTFE layer. FIGS. 9 to 13 illustrate a PTFE film 110 having a closed microstructural network and that is substantially impermeable to liquid and gas; other embodiments of PTFE layers may be manufactured using the methods discussed herein to have other suitable permeability values and pore sizes.

PTFE film 110 may have an average thickness that is less than about 0.005 inch, specifically from about 0.00005 inch to about 0.005 inch, and more specifically from about 0.0001 inch to about 0.002 inch.

While embodiments of methods discussed herein are directed to manufacturing PTFE layers, it should be appreciated that the methods discussed may also be useful in the manufacture of other fluoropolymer-based films having substantial, low or substantially no fluid permeability. As such, the methods discussed herein are not limited to the processing of PTFE materials. For example, the processing of other fluoropolymer resin-based materials, such as copolymers of tetrafluororethylene and other monomers, is also contemplated.

Figure 14:
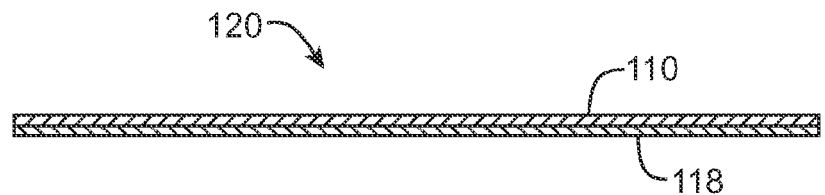
FIG. 14 schematically illustrates a composite PTFE film that comprises a PTFE layer having low or substantially no fluid permeability and a porous PTFE layer.

The PTFE layers and PTFE films may be used in a variety of ways. For example, the PTFE layer and PTFE film embodiments of the present invention may be used for prosthetic devices such as a vascular graft, breast implants and the like. Other applications include tubing, protective clothing, insulation, sports equipment, filters, membranes, fuel cells, ionic exchange barriers, gaskets as well as others. Referring now to FIG. 14, PTFE layer 110 may be combined with, bonded to, or otherwise coupled, affixed or attached, partially or completely, to at least one additional layer 118 to form a composite film 120. Depending on the use of composite film 120, layer 118 may be chosen to have properties that combine with the properties of layer 110 to give the desired properties in composite film 120. The additional layer 118 may include a porous PTFE layer, a substantially non-porous PTFE layer, an air or liquid permeable PTFE layer, an air- or liquid-impermeable layer, an ePTFE layer, a non-expanded PTFE layer, a fluoropolymer layer, a non-fluoropolymer layer, or any combination thereof. In one embodiment, layer 118 is a porous, fluid permeable, expanded PTFE layer having a conventional node and fibril microstructure. If desired, one or more reinforcing layers (not shown) optionally may be coupled to the composite PTFE film 120. The reinforcing layer may be disposed between layers 110 or 118, or the reinforcing layer(s) may be coupled to an exposed surface of PTFE layer 110, PTFE layer 118, or both. PTFE layer 110 and layer 118 may be combined, bonded to, or otherwise coupled, affixed or attached, partially or completely, to one another using any suitable method known in the art. For example, an adhesive may be used to selectively bond at least a portion of layers 110 and 118 to each other. Alternatively, heat fusion, pressure bonding, sintering, and the like may be used to bond at least a portion of layers 110 and 118 to each other.

Figure 15:
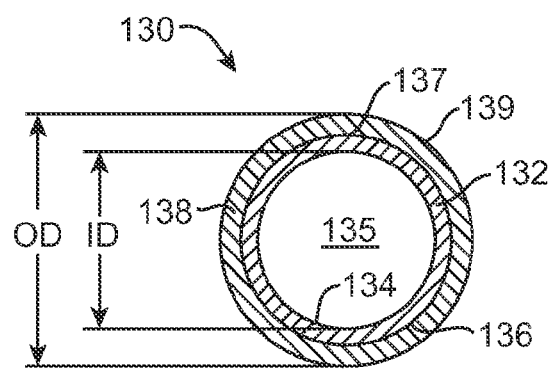
FIG. 15 schematically illustrates a simplified tubular structure that comprises an outer layer having low or substantially no fluid permeability and a fluid-permeable inner layer.
Figure 16:
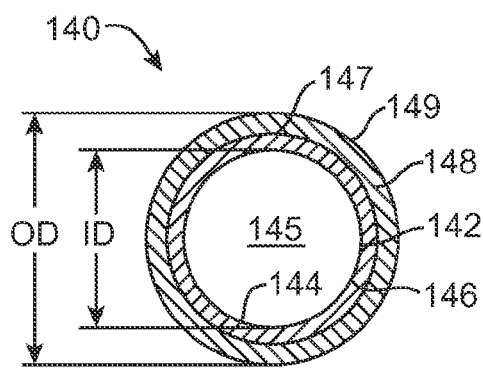
FIG. 16 schematically illustrates a simplified tubular structure that comprises a layer having low or substantially no fluid permeability and a fluid-permeable outer layer.

FIGS. 15 and 16 are transverse cross-sectional views of two composite tubular structures 130 and 140, respectively. Tubular structures 130 and 140 may be a portion or section of an endovascular graft or the like. As shown in FIG. 15, tubular structure 130 includes an inner tubular body 132 that comprises an inner surface 134 and an outer surface 136. Tubular body 132 may comprise one or more layers of fluid-permeable PTFE. Such a fluid-permeable layer of PTFE may have a Gurley measurement of less than about 10 Gurley seconds. Tubular structure 130 further comprises an outer tubular body 138 that comprises an inner surface 137 and an outer surface 139. Inner surface 137 of outer tubular body 138 is coupled to the outer surface 136 of the inner tubular body 132. Tubular body 138 may comprise one or more PTFE layers having low fluid-permeability or substantially no fluid-permeability. In this configuration, inner surface 134 of the tubular body 132 defines an inner lumen 135 of tubular structure 130 and the outer surface 139 of the tubular body 138 defines an outer surface 139 of the tubular structure 130. Tubular body 138 may be combined, bonded to, or otherwise coupled, affixed or attached, partially or completely, to the tubular body 132 through any suitable method known in the art. For example, an adhesive may be used to selectively bond at least a portion of tubular body 138 and tubular body 132 to each other. Alternatively, heat fusion, pressure bonding, sintering, and the like, or any combination thereof, may be used to bond at least a portion of tubular body 138 and tubular body 132 to each other.

As shown in FIG. 16, tubular structure 140 includes an inner tubular body 142 that comprises an inner surface 144 and an outer surface 146. Tubular body 142 may comprise one or more layers of PTFE having low or substantially no fluid permeability. Tubular structure 140 further comprises an outer tubular body 148 that comprises an inner surface 147 and an outer surface 149. Inner surface 147 of outer tubular body 148 is coupled to the outer surface 146 of the inner tubular body 142. Outer tubular body 148 may comprise one or more layers of fluid-permeable PTFE. Embodiments of fluid-permeable layers of PTFE may have a Gurley measurement of less than about 10 Gurley seconds. In this configuration, inner surface 144 of the inner tubular body 142 defines an inner lumen 145 of tubular structure 140 and the outer surface 149 of the outer tubular body 148 defines an outer surface 149 of the tubular structure 140. Tubular body 148 may be combined, bonded to, or otherwise coupled, affixed or attached, partially or completely, to the tubular body 142 through any suitable method known in the art. For example, an adhesive may be used to selectively bond at least a portion of tubular body 148 and tubular body 132 to each other. Alternatively, heat fusion, pressure bonding, sintering, and the like, or any combination thereof, may be used to bond at least a portion of tubular body 148 and tubular body 142 to each other.

Tubular structures 130 or 140 may define an inner diameter ID which is the diameter of the inner surface, which may define the area of flow through tubular structure 130 or 140. An outer diameter OD, which is the diameter of the outer surface 139 or 149 of the outer tubular layer 138 or 148. The inner diameter ID and outer diameter OD may be any desired diameter. For use in an endovascular graft, the inner diameter ID but is typically from about 10 mm to about 40 mm and the outer diameter OD is typically from about 12 mm to about 42 mm. The tubular layers may have any suitable thickness, however, fluid-impermeable PTFE layers 138 and 142 have a thickness from about 0.0005 inch and about 0.01 inch thick, and specifically from about 0.0002 inch to about 0.001 inch. Similarly, fluid-permeable PTFE layers 132 or 148 may also be any thickness desired, but typically have a thickness from about 0.0001 inch and about 0.01 inch, and specifically from about 0.0002 inch to about 0.001 inch. As can be appreciated, the thicknesses and diameters of the tubular structures 130 or 140 will vary depending on the use of the tubular structures.

Tubular structures 130 or 140 may be formed as tubes through conventional tubular extrusion processes. Typically, however, tubular structures 130 or 140 may be formed from PTFE layers 110 or 118, as shown in FIG. 14, that are folded on a shape forming mandrel over each other so that ends of the layers are overlapped and bonded (not shown). As another alternative, PTFE layers 110 or 118 may be helically wound about the shape forming mandrel to form the tubular structure. Some exemplary methods of forming a tubular PTFE structure is described in commonly owned U.S. patent application Ser. No. 10/029,557 (which published as U.S. Patent Application No. 2003/0116260 A1) and entitled "Methods and Apparatus for Manufacturing an Endovascular Graft Section", Ser. No. 10/029,584 (which published as U.S. Pat. No. 7,090,693) and entitled "Endovascular Graft Joint and Method of Manufacture", both filed on Dec. 20, 2001 to Chobotov et al., and U.S. Pat. No. 6,776,604 to Chobotov et al., the complete disclosures of which are incorporated herein by reference.

The films and layers discussed herein are not limited to a single porous PTFE layer 118 and a single PTFE layer or film 110 having low or substantially no fluid permeability. The composite films 120 and tubular structures 130 or 140 may include a plurality of porous fluid permeable PTFE layers (having the same or different node and fibril size and orientation, porosity, pore size, and the like), one or more non-porous, densified PTFE layers, and/or one or more PTFE layers 110 having low or substantially no fluid permeability. For example, PTFE layer 110 having low or substantially no fluid permeability may be disposed between an inner and outer porous PTFE film or layer. The inner and outer porous PTFE layers may have varying porosities or the same porosities. In such embodiments, the PTFE layer 110 may have a reduced thickness relative to the porous PTFE layers. In other embodiments, however, the PTFE layer 110 may have the same thickness or larger thickness than the porous PTFE layers. As an alternative embodiment to FIGS. 15 and 16, tubular structures 130 or 140 may comprise inner and outer tubular bodies that both have low or substantially no fluid permeability.

Figure 17:
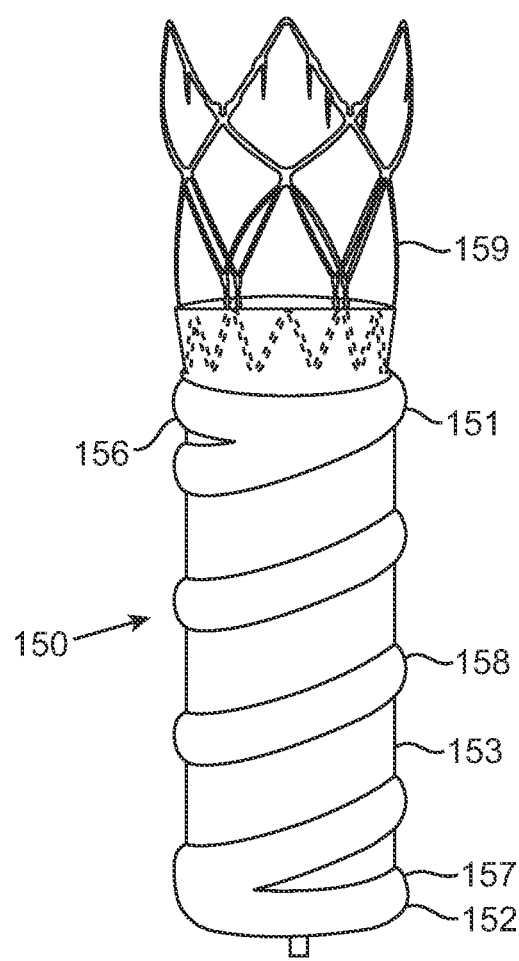
FIG. 17 illustrates an embodiment of an endovascular graft having a network of inflatable conduits.

Referring now to FIG. 17, a tubular structure that is in the form of an inflatable endovascular graft 50 is shown. For the purposes of this application, with reference to endovascular graft devices, the term "proximal" describes the end of the graft that will be oriented towards the oncoming flow of bodily fluid, typically blood, when the device is deployed within a body passageway. The term "distal" therefore describes the graft end opposite the proximal end. Graft 150 has a proximal end 151 and a distal end 152 and includes a generally tubular structure or graft body section 153 comprised of one or more layers of fusible material, including such materials as PTFE and ePTFE. The inner surface of the tubular structure defines an inner diameter and acts as a luminal surface for flow of fluids therethrough. The outer surface of the tubular structure defines an abluminal surface that is adapted to be positioned adjacent the body lumen wall, within the weakened portion of the body lumen, or both. Note that although FIG. 17 shows an inflatable endovascular graft, the layers and films of the present invention may be used in non-inflatable endovascular grafts as well, in addition to other medical and non-medical applications.

A proximal inflatable cuff 156 may be disposed at or near a proximal end 151 of graft body section 153 and a distal inflatable cuff 157 may be disposed at or near a graft body section distal end 152. Graft body section 153 forms a longitudinal lumen that is configured to confine a flow of fluid, such as blood, therethrough. Graft 150 may be manufactured to have any desired length and internal and external diameter but typically ranges in length from about 5 cm to about 30 cm; specifically from about 10 cm to about 30 cm. If desired, a stent 159 may be attached at the proximal end 151 and/or the distal end 152 of the graft 150. Depending on the construction of the cuffs 156 and 157 and graft body section 153, inflation of cuffs 156 and 157, when not constrained (such as, e.g., by a vessel or other body lumen), may cause the cuffs 156 and 157 to assume a generally annular or toroidal shape with a generally semicircular longitudinal cross-section. Inflatable cuffs 156 and 157 may be designed to generally, however, conform to the shape of the vessel within which it is deployed. When fully inflated, cuffs 156 and 157 may have an outside diameter ranging from about 10 mm to about 45 mm; specifically from about 16 mm to about 42 mm.

At least one inflatable channel 158 may be disposed between and in fluid communication with proximal inflatable cuff 156 and optional distal inflatable cuff 157. Inflatable channel 158 in the FIG. 17 example has a helical configuration and provides structural support to graft body section 153 when inflated to contain an inflation medium. Inflatable channel 158 further prevents kinking and twisting of the tubular structure or graft body section when it is deployed within angled or tortuous anatomies as well as during remodeling of body passageways, such as the aorta and iliac arteries, within which graft 150 may be deployed. Together with proximal and distal cuffs 156 and 157, inflatable channel 158 forms an inflatable network over the length of the body 153. Depending on the desired characteristics of the endovascular graft 150, at least one layer of the graft may be a PTFE layer having low or substantially no fluid permeability such as PTFE layer or film 110. The PTFE layer may be one of the layers that forms the inflatable channels 158, or the PTFE layer may surround or be underneath the inflatable channel 158 and cuffs 156 and 157.

Graft body 153 may be formed of two or more layers or strips of PTFE that are selectively fused or otherwise adhered together as described herein, to form the inflatable cuffs 156 and 157 and inflatable channel 158 therebetween. A detailed description of some methods of manufacturing a multi-layered graft are described in commonly owned U.S. patent application Ser. No. 10/029,557 (which published as U.S. Patent Application Publication No. 2003/0116260 A1), Ser. No. 10/029,584 (which published as U.S. Pat. No. 7,090,693), U.S. patent application Ser. No. 10/168,053 (which published as U.S. Pat. No. 8,226,708), filed Jun. 14, 2002 and entitled "Inflatable Intraluminal Graft" to Murch, and U.S. Pat. No. 6,776,604 to Chobotov et al., the complete disclosures of which are incorporated herein by reference.

FIGS. 18 to 21 illustrate transverse cross sectional views of different embodiments of inflatable channel 158. As can be appreciated, the embodiments of FIGS. 18 to 21 may also be applicable to the proximal and distal cuffs 156 and 157. Inflatable channel 158 defines an inflatable space 162 that is created between an inner layer 164 and outer layer 166. If desired an inflation medium 167 may be delivered into the space 162 to inflate inflatable space 162. Inflation medium 167 optionally may include a deliverable agent 168 as shown in FIGS. 18 to 21, such as a therapeutic agent 168 that may be configured to be diffused in a controlled manner or otherwise transmitted through pores (not shown) in inner layer 164, outer layer 166 or both. The embodiments shown in FIGS. 18-21 are merely exemplary, as it may be desirable to have preferential diffusion of the deliverable agent 168 through layer 164 or layer 166. In addition, both layers 164 and 166 may be configured to allow a significant amount of diffusion of deliverable agent 168, but with one of the two layers having a greater permeability to the deliverable agent 168 than the other layer. While inner layer 164 and layer 166 are shown as having only a single layer of material, it should be appreciated that each of layers 164 or 166 may include one or more layers to form a composite film of fluid-permeable PTFE, PTFE having low fluid permeability, PTFE having substantially no fluid permeability or any combination thereof. A more complete description of methods and devices for the delivery of a therapeutic agent can be found in commonly owned U.S. patent application Ser. No. 10/769,532 (which published as U.S. Patent Application Publication No. 2005/0171593 A1), filed Jan. 30, 2004 and entitled "Inflatable Porous Implants and Methods for Drug Delivery" to Whirley et al., the complete disclosure of which is incorporated herein by reference. A description of exemplary inflation medium materials can be found in commonly owned U.S. patent application Ser. No. 11/097,467 (which published as U.S. Patent Application Publication No. 2006-0222596 A1), filed Apr. 1, 2005 and entitled "A Non-Degradable, Low Swelling, Water Soluble, Radiopaque Hydrogel" to Askari et al., the complete disclosure of which is incorporated herein by reference.

Figure 18:
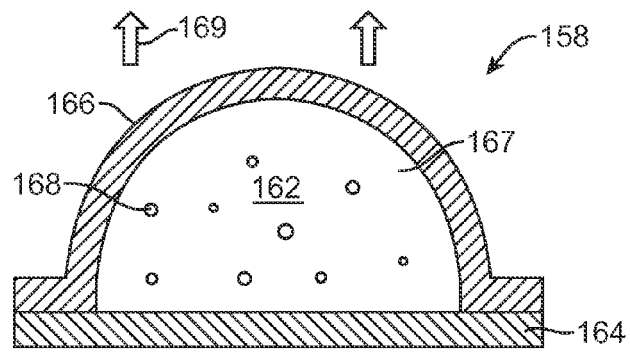
FIGS. 18 to 20 are transverse cross sectional views of an inflatable conduit of the graft of FIG. 17.

In the embodiment shown in FIG. 18, outer layer 166 is permeable to fluids so as to allow the therapeutic agent 168, which may be a liquid, to diffuse over time in the direction of arrow 169 through outer layer 166. In such embodiments, inner layer 164 typically has a low or substantially no fluid permeability, and could therefore be considered a "barrier layer." Because the inner "barrier" layer 164 has low or substantially no fluid permeability and outer layer 166 is fluid permeable, the therapeutic agent will preferentially diffuse from space 162 in the direction of arrow 169. The use of one (or more) porous fluid permeable outer PTFE layers and an inner layer 164 having low or substantially no fluid permeability provides for improved release of a therapeutic agent through liquid permeable outer layer 166. Varying the porosity or pore size across at least a portion of outer layer 166 may provide even more localized delivery of the therapeutic agent 168 through outer layer 166.

Figure 19:
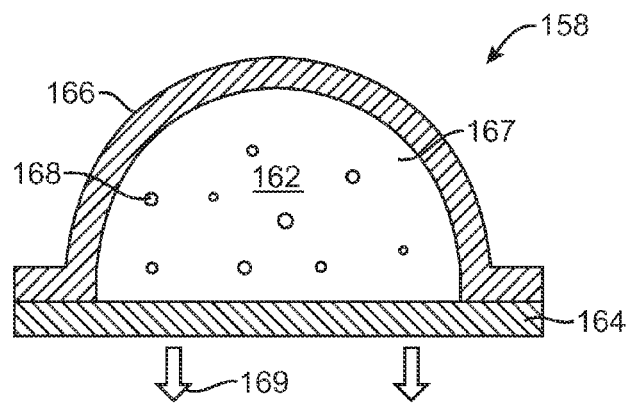

In an alternative configuration shown in FIG. 19, inner layer 164 may be substantially fluid-permeable to allow the therapeutic agent 168 to selectively diffuse in the direction of arrow 169 through inner layer 164 and into the lumen of the tubular structure (e.g., lumen 135, 145 of FIGS. 15 and 16). In such embodiments, outer layer 166 typically has no or substantially no fluid-permeability and acts as a "barrier layer." As such, the therapeutic agent will preferentially diffuse from space 162 in the direction of arrow 169. The use of porous fluid permeable PTFE layers and outer layer 166 having low or substantially no fluid permeability provides for improved release of a therapeutic agent into the inner lumen through fluid permeable inner layer 164. Varying the permeability and/or porosity or pore size across at least a portion of inner layer 164 may provide even more localized delivery of the therapeutic agent 168 through layer 164.

Figure 20:
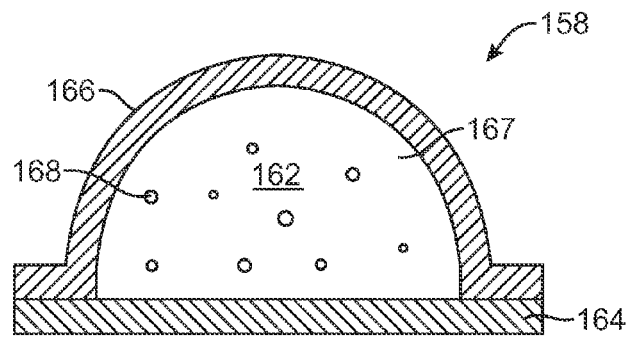
Figure 21:
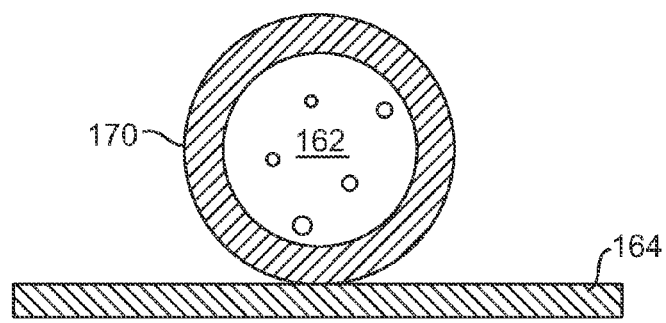
FIG. 21 is a transverse cross sectional view of an embodiment of a tubular inflatable conduit.

As shown in FIG. 20, if it is desired to prevent the inflation medium 167 from escaping from inflatable space 162, both the inner layer 164 and outer layer 166 may comprise a "barrier" layer having low or substantially no fluid permeability. In such embodiments, the inner and outer layers 164 and 166 have low or substantially no fluid permeability. In such embodiments, inflation material 167 typically will not contain a therapeutic agent. Referring to FIG. 21, the inflatable channel may be a substantially tubular channel 170 that is fused or otherwise adhered to layer 164 that defines a portion of the graft. If delivery of a therapeutic agent is desired, tubular channel 170 will be liquid-permeable and will allow diffusion of the therapeutic agent 168 through pores in tubular channel 170. In some embodiments, by varying the permeability and/or porosity or pore size across at least a portion of channel 170 may provide a localized delivery of the therapeutic agent 168 selected portions of channel 170. If however, it is desired to prevent the inflation fluid 167 from escaping from inflatable space 162, then tubular channel 170 will act as a barrier layer and may comprise at least one layer of PTFE having low or substantially no fluid permeability.

Figure 22:
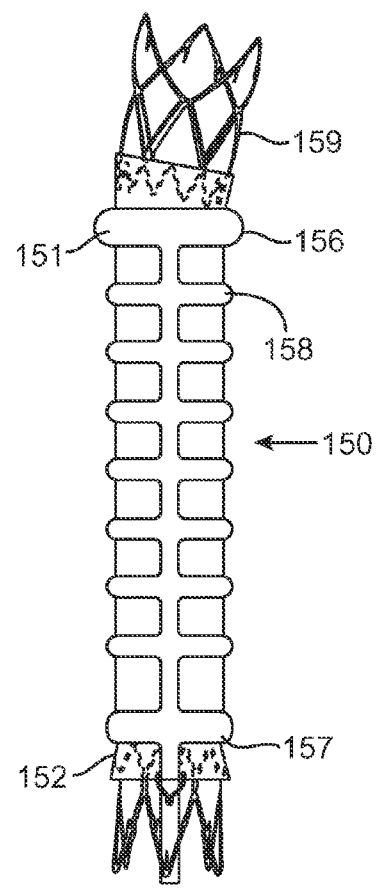
FIG. 22 is an elevational view that illustrates another embodiment of an inflatable endovascular graft.
Figure 23:
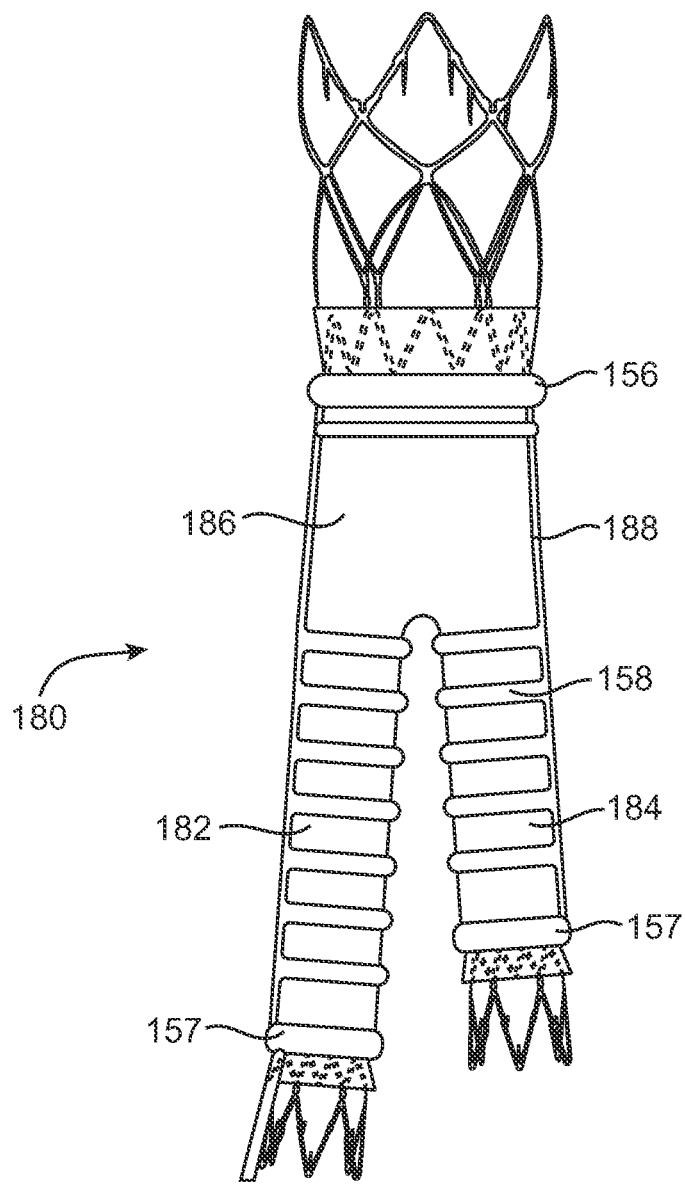
FIG. 23 illustrates an embodiment of an inflatable bifurcated endovascular graft.

Referring now to FIGS. 22 and 23, the respective graft embodiments 150 and 180 shown include an inflatable channel 158 has portions with a circumferential configuration as opposed to the helical configuration of the inflatable channel 158 shown in FIG. 17. The circumferential configuration of portions of the inflatable channel 158 may be particularly effective in providing the needed kink resistance for endovascular graft for effectively treating diseased body passageways such as a thoracic aortic aneurysm (TAA), abdominal aortic aneurysm (AAA), in which highly angled and tortuous anatomies are frequently found. In alternative embodiments, other cuff and channel configurations are possible. Inflatable channel 158 may be configured circumferentially as shown in FIGS. 22 and 23.

In addition to the substantially tubular grafts of FIG. 22, bifurcated endovascular grafts as shown in FIG. 23, are also contemplated. The bifurcated endovascular graft 180 may be utilized to repair a diseased lumen at or near a bifurcation within the vessel, such as, for example, in the case of an abdominal aortic aneurysm in which the aneurysm to be treated may extend into the anatomical bifurcation or even into one or both of the iliac arteries distal to the bifurcation. In the following discussion, the various features of the graft embodiments previously discussed may be used as necessary in the bifurcated graft 80 embodiment unless specifically mentioned otherwise.

Graft 180 comprises a first bifurcated portion 182, a second bifurcated portion 184 and main body portion 186. The size and angular orientation of the bifurcated portions 182 and 184 may vary to accommodate graft delivery system requirements and various clinical demands. The size and angular orientation may vary even between portion 182 and 184. For instance, each bifurcated portion or leg is shown in FIG. 23 to optionally have a different length. First and second bifurcated portions 182 and 184 are generally configured to have an outer inflated diameter that is compatible with the inner diameter of a patient's iliac arteries. First and second bifurcated portions 182 and 184 may also be formed in a curved shape to better accommodate curved and even tortuous anatomies in some applications. Together, main body portion 186 and first and second bifurcated portions 182 and 184 form a continuous bifurcated lumen, similar to the inner lumens of FIG. 22, which is configured to confine a flow of fluid therethrough. A complete description of some desirable sizes and spacing of inflatable channels may be found in commonly owned U.S. patent application Ser. No. 10/384,103 (which published as U.S. Patent Application Publication No. 20040176836 A1), entitled "Kink-Resistant Endovascular Graft" and filed Mar. 6, 2003 to Kari et al., the complete disclosure of which is incorporated herein by reference.

While not shown, it should be appreciated, that instead of circumferential channels and longitudinal channels, the bifurcated graft 180 may comprise a helical inflatable channel 158, similar to that of the graft embodiment shown in FIG. 17 (or other channel geometries to achieve desired results), or a combination of helical and circumferential channels. A complete description of some embodiments of endovascular grafts that have helical and cylindrical channel configurations may be found in co-pending and commonly owned U.S. patent application Ser. No. 10/384,103 (which published as U.S. Patent Application Publication No. 20040176836 A1). Other endovascular grafts that the liquid-impermeable PTFE film may be used with are described in U.S. Pat. No. 6,395,019 to Chobotov, U.S. Pat. No. 6,132,457 to Chobotov, U.S. Pat. No. 6,331,191 to Chobotov, and U.S. patent application Ser. No. 10/327,711 (which published as U.S. Patent Application Publication No. 2003/0125797 A1), entitled "Advanced Endovascular Graft" to Chobotov et al. and filed Dec. 20, 2002, Ser. No. 10/168,053 (which published as U.S. Pat. No. 8,226,708), the complete disclosures of which are incorporated herein by reference.

As can be appreciated, the inflatable portions of the graft 180 optionally may be configured to have varying levels of fluid permeability and/or porosity, either within or between particular cuffs, channels or cuff/channel segments, so as to provide for controlled drug delivery, programmed drug delivery or both, into the vessel wall or lumen of the graft via elution of the agent from pores in the layers. For example, any desired portion of the graft 180 may include PTFE layers having low or substantially no fluid permeability. Such a configuration would be useful in applications in which the drug delivery rate and other properties of the graft or stent-graft (e.g. mechanical properties) may be selected for the particular clinical needs and indication that is contemplated for that device. In addition, the fluid permeability and/or porosity may be uniform within a particular cuff or channel but different between any given channel and/or cuffs. In addition to improved drug delivery, the variable porosity of the outer surface of the graft may also be beneficial for promoting tissue in-growth into the graft. It may be possible to make portions of the graft that are in direct contact with the body lumen to have a higher porosity and/or larger pore size so as to promote tissue in-growth. In particular, tissue in-growth may be beneficial adjacent to the proximal and distal ends of the graft.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The following listing of embodiments are useful with the present invention:

Embodiment 1

A method of processing PTFE, comprising:
providing a layer of PTFE;
applying a stretching agent to at least a portion of the layer of PTFE; and
stretching the layer of PTFE while the layer of PTFE is wet with the stretching agent to form a stretched layer of PTFE.

Embodiment 2

The method of embodiment 1 wherein the stretching agent is applied to substantially all of the layer of PTFE prior to stretching.

Embodiment 3

The method of embodiment 1 wherein stretching the layer of PTFE comprises stretching the layer of PTFE by a stretch ratio of about 2:1 to about 20:1.

Embodiment 4

The method of embodiment 1 wherein the stretching of the layer of PTFE comprises stretching in a machine direction.

Embodiment 5

The method of embodiment 1 wherein the stretching of the layer comprises stretching the layer of PTFE in a direction transverse to the machine direction.

Embodiment 6

The method of embodiment 1 further comprising calendering the stretched layer of PTFE to densify and compress the layer of PTFE.

Embodiment 7

The method of embodiment 1 wherein the stretching agent comprises an isoparaffin.

Embodiment 8

The method of embodiment 1 wherein the stretching agent is selected from the group consisting of naphtha, mineral spirits, alcohol, MEK, toluene and alcohol.

Embodiment 9

The method of embodiment 1 wherein a lubricant content of the layer of PTFE prior to application of the stretching agent is about 0 percent by weight to about 22 percent by weight.

Embodiment 10

The method of embodiment 1 further comprising spreading the stretching agent after application to the layer of PTFE with a skimming member disposed adjacent the layer of PTFE.

Embodiment 11

The method of embodiment 1 wherein stretching of the layer of PTFE is performed at a temperature of about 80° F. to about 100° F.

Embodiment 12

The method of embodiment 1 wherein stretching of the layer of PTFE is performed at a temperature of about 85° F. to about 95° F.

Embodiment 13

The method of embodiment 1 wherein the stretching agent is applied to the layer of PTFE at a temperature of about 110° F. to about 130° F.

Embodiment 14

The method of embodiment 13 wherein the stretching agent is applied to the layer of PTFE at a temperature of about 115° F. to about 125° F.

Embodiment 15

The method of embodiment 1 wherein stretching the layer of PTFE is performed at a temperature that is just above the glass transition temperature of the PTFE layer material.

Embodiment 16

The method of embodiment 1 wherein the provided layer of PTFE is produced by extruding a compounded PTFE resin through an extruder to form a PTFE ribbon extrudate.

Embodiment 17

The method of embodiment 16 wherein the compounded resin is extruded to an extrudate having a ribbon configuration and having a thickness of about 0.020 inch to about 0.040 inch.

Embodiment 18

The method of embodiment 16 wherein the PTFE ribbon extrudate is calendered to a reduced thickness of about 0.001 inch to about 0.005 inch prior to stretching.

Embodiment 19

The method of embodiment 1 wherein the stretching agent is applied to the layer of PTFE in sufficient quantity such that at least a portion of the layer of PTFE is saturated with stretching agent at the time of stretching.

Embodiment 20

The method of embodiment 1 further comprising stretching the stretched layer of PTFE a second time with no stretching agent added to the stretched layer of PTFE during the second stretch.

Embodiment 21

The method of embodiment 20 wherein the stretched layer of PTFE has a sufficiently low stretching agent content so to form a discernable node and fibril microstructure in the stretched layer of PTFE during the second stretch.

Embodiment 22

The method of embodiment 1 further comprising sintering the stretched layer of PTFE.

Embodiment 23

A method of processing PTFE, comprising:
  providing a layer of PTFE;
  applying a stretching agent to at least a portion of the layer of PTFE until a portion of the layer of PTFE is saturated with the stretching agent to form a saturated portion; and
  stretching the layer of PTFE while the saturated portion of the layer of PTFE is saturated with the stretching agent.

Embodiment 24

The method of embodiment 23 wherein substantially all of the layer of PTFE is saturated with stretching agent to form a saturated portion prior to stretching.

Embodiment 25

The method of embodiment 24 further comprising sintering the layer of PTFE.

Embodiment 26

A method of processing PTFE, comprising:
providing a stretched layer of PTFE that has been stretched in at least a first direction;
applying a stretching agent to at least a portion of the stretched layer of PTFE; and
stretching the stretched layer of PTFE while the stretched layer of PTFE is wet with the stretching agent.

Embodiment 27

The method of embodiment 26 wherein the stretching agent is applied to substantially all of the stretched layer of PTFE prior to the stretching of the stretched layer.

Embodiment 28

The method of embodiment 26 wherein the stretched layer of PTFE has a lubricant content of below about 3% by weight prior to application of the stretching agent.

Embodiment 29

The method of embodiment 26 wherein the stretched layer of PTFE has been stretched in the first direction with a sufficiently low stretching agent content so to form a discernable node and fibril microstructure in the stretched layer of PTFE during the stretch in the first direction.

Embodiment 30

The method of embodiment 26 wherein the stretching of the stretched layer is performed in a direction different than the first direction.

Embodiment 31

The method of embodiment 30 wherein the first direction is a machine direction and the stretching of the stretched layer is performed in a transverse direction.

Embodiment 32

The method of embodiment 30 wherein the stretching of the stretched layer of PTFE material is performed in a transverse direction by a stretch ratio of about 2:1 to about 30:1.

Embodiment 33

The method of embodiment 26 wherein the stretching of the stretched layer is performed in substantially the same direction as the first direction.

Embodiment 34

The method of embodiment 33 wherein the first direction is a machine direction and the stretching of the stretched layer is performed in the machine direction.

Embodiment 35

The method of embodiment 26 wherein the stretched layer of PTFE has been stretched in the first direction while the layer of PTFE was wet with stretching agent applied to the layer of PTFE.

Embodiment 36

The method of embodiment 26 further comprising sintering the layer of PTFE.

Embodiment 37

A method of processing PTFE, comprising:
providing a layer of PTFE;
applying a stretching agent to at least a portion of the layer;
stretching the layer of PTFE while the layer of PTFE is wet with the stretching agent to form a stretched layer of PTFE;
stretching the stretched layer of PTFE a second time; and
calendering the twice-stretched layer of PTFE so as to densify and further thin the twice-stretched layer of PTFE.

Embodiment 38

The method of embodiment 37 wherein the stretching agent is applied to substantially all of the surface of the layer prior to stretching.

Embodiment 39

A PTFE layer comprising a layer made by
providing a layer of PTFE;
applying a stretching agent to a surface of the layer; and
stretching the layer of PTFE while the layer of PTFE is wet with the stretching agent.

Embodiment 40

A PTFE layer comprising a layer made by
providing a layer of PTFE;
applying a stretching agent to a surface of the layer;
stretching the layer of PTFE while the layer of PTFE is wet with the stretching agent; and
stretching the stretched layer of PTFE a second time.

Embodiment 41

A PTFE layer comprising a layer made by
providing a layer of PTFE;
applying a stretching agent to a surface of the layer;
stretching the layer of PTFE while the layer of PTFE is wet with the stretching agent;
stretching the stretched layer of PTFE a second time; and
calendering the twice-stretched layer of PTFE so as to densify and further thin the twice-stretched layer of PTFE.

Embodiment 42

A thin PTFE layer comprising substantially low porosity, low permeability, no discernable node and fibril structure, and having a thickness of about 0.00005 inch to about 0.005 inch.

Embodiment 43

A composite PTFE film comprising:
a first layer comprising a stretched layer of PTFE that has a closed cell microstructure with a plurality of interconnected high density regions having no discernable node and fibril microstructure between the high density regions; and
a second layer of expanded PTFE which is secured to the first layer and which includes a substantial node and fibril microstructure.

Embodiment 44

A thin, substantially liquid-impermeable PTFE layer produced by:
providing a PTFE layer;
adding a stretching agent to the PTFE layer; and
stretching the PTFE layer in at least one direction to reduce a thickness of the PTFE layer without substantially creating a liquid permeability in the stretched PTFE layer.

Embodiment 45

The thin layer of embodiment 41 wherein the stretched PTFE layer comprises a closed cell microstructure that comprises a plurality of interconnected high density regions with no discernable node and fibril microstructure.

Embodiment 46

A multi-layered vascular graft comprising:
a first tubular body having an outer surface and an inner surface that defines an inner lumen of the vascular graft; and
a second tubular body having an outer surface and an inner surface coupled to the outer surface of the first tubular body,
wherein one of the first tubular body and the second tubular body comprises a fluid-permeable PTFE layer and the other tubular body comprises a PTFE layer having low fluid permeability.

Embodiment 47

The multi-layered vascular graft of embodiment 46 wherein the PTFE layer having low fluid permeability comprises a closed cell microstructure that comprises a plurality of interconnected high density regions wherein the closed cell microstructure has no discernable node and fibril microstructure.

Embodiment 48

The multi-layered vascular graft of embodiment 46 wherein the PTFE layer having low fluid permeability comprises a thin PTFE layer having substantially low porosity, no discernable node and fibril structure, and a high degree of limpness and suppleness so to allow mechanical manipulation or strain of the PTFE layer without significant recoil or spring back.

Embodiment 49

An inflatable endovascular graft comprising a body portion having an inflatable channel that defines an inflatable space, wherein the inflatable space is at least partially surrounded by a thin, PTFE layer having substantially no fluid permeability.

Embodiment 50

The inflatable endovascular graft of embodiment 49 wherein the PTFE layer having substantially no fluid permeability comprises a closed cell microstructure that comprises a plurality of interconnected high density regions and wherein the closed cell microstructure has no discernable node and fibril microstructure.

Embodiment 51

The inflatable endovascular graft of embodiment 49 wherein the PTFE layer having substantially no fluid permeability comprises a thin PTFE layer having substantially low porosity, no discernable node and fibril structure, and a high degree of limpness and suppleness to allow mechanical manipulation or strain of the PTFE layer without significant recoil or spring back.

Embodiment 52

A stretched, PTFE layer that comprises a closed cell microstructure having high density regions whose grain boundaries are directly interconnected to grain boundaries of adjacent high density regions and having no discernable node and fibril microstructure and having substantially no fluid permeability.

Embodiment

A composite film comprising a fluid-permeable, expanded PTFE layer secured to a surface of a thin stretched PTFE layer having a closed cell microstructure having high density regions whose grain boundaries are directly interconnected to grain boundaries of adjacent high density regions and having no discernable node and fibril microstructure.

Embodiment 54

A tubular structure comprising a composite film comprising a fluid-permeable, expanded PTFE layer secured to a surface of a thin, stretched PTFE layer having a closed cell microstructure having high density regions whose grain boundaries are directly interconnected to grain boundaries of adjacent high density regions and having no discernable node and fibril microstructure.

Embodiment 55

An endovascular graft comprising a composite film with a fluid-permeable, expanded PTFE layer secured to a surface of a thin stretched PTFE layer having a closed cell microstructure having high density regions whose grain boundaries are directly interconnected to grain boundaries of adjacent high density regions and having no discernable node and fibril microstructure.

Embodiment 56

A thin PTFE layer, comprising substantially low porosity, low liquid permeability, no discernable node and fibril structure, and a high degree of limpness and suppleness so to allow mechanical manipulation or strain of the PTFE layer without significant recoil or spring back.

Embodiment 57

A thin layer of PTFE comprising a stretched layer of PTFE that has a closed cell microstructure with a plurality of interconnected high density regions having no discernable node and fibril microstructure between the high density regions.

Embodiment 58

A method of controlling the porosity, density or both of a PTFE layer, comprising:
stretching the PTFE layer at least one time at a preselected temperature while using a preselected stretching agent content for the at least one stretch.

What is claimed is:

1. A method of processing PTFE, comprising:
extruding a compounded PTFE resin through an extruder in a machine direction to form a PTFE ribbon extrudate;
calendering the PTFE ribbon extrudate in the machine direction to form a layer of PTFE having an upper surface, a lower surface and a longitudinal length in a machine direction of an extruder used to produce the layer of PTFE and having a width in a cross machine or transverse direction;
applying a liquid stretching agent in an excess amount to at least a portion of the upper surface or the lower surface of the layer of PTFE;
stretching the layer of PTFE in the transverse direction to the machine direction; and
maintaining the excess amount of the liquid stretching agent on the at least portion of the upper or the lower surface of the layer of PTFE during at least part of the stretching to fully saturate the layer of PTFE throughout its thickness with the liquid stretching agent during the stretching to form a stretched layer of PTFE that has:
(i) a closed cell microstructure with a plurality of interconnected high density regions of PTFE having no distinct fibrils interconnecting adjacent nodes when viewed at a magnification of 20,000 under a scanning electron microscope; and
(ii) a thickness from 0.00005 inch to 0.005 inch;
wherein the stretching is at a rate from 10 percent per second to 100 percent per second;
wherein the stretching is performed at a stretch ratio from 2:1 to 20:1; and
wherein stretching of the layer of PTFE is performed at a temperature of 80° F. to 100° F.

2. The method of claim 1 wherein the stretching is performed at a stretch ratio from 3:1 to 20:1.

3. The method of claim 1 wherein the stretching is performed at a stretch ratio from 3:1 to 12:1.

4. The method of claim 1 wherein the stretching is performed at a stretch ratio from 3:1 to 7.8:1.

5. The method of claim 1 wherein the step of applying the liquid stretching agent on the upper surface of the layer of PTFE further compromises:
pooling or puddling the upper surface of the layer of PTFE with the liquid stretching agent.

6. The method of claim 1 further comprising spreading the liquid stretching agent after application to the layer of PTFE with a skimming member disposed adjacent the upper or the lower surface of the layer of PTFE.

7. The method of claim 1 wherein the liquid stretching agent is applied to substantially all of the upper or the lower surface of the layer of PTFE prior to stretching.

8. The method of claim 1 wherein the stretched layer of PTFE, after sintering at a temperature from about 350° C. to about 380° C. for about 2 minutes to about 5 minutes, has substantially no fluid permeability with a Gurley Number of greater than 12 hours for 100 cc of air at a pressure of 12.4 cm of water.

9. The method of claim 1 wherein the stretched layer of PTFE has a limited fluid permeability with a Gurley Number of greater than 1,500 seconds for 100 cc of air at a pressure of 12.4 cm of water.

10. The method of claim 1 wherein the stretched layer of PTFE has a range of permeability from substantially no fluid permeability with a Gurley Number of greater than 12 hours for 100 cc of air at a pressure of 12.4 cm of water to a limited permeability with a Gurley Number of less than 1,500 seconds for 100 cc of air at a pressure of 12.4 cm of water.

11. The method of claim 1 wherein the liquid stretching agent is selected from the group consisting of naphtha, mineral spirits, MEK, toluene and alcohol.

12. The method of claim 1 wherein the liquid stretching agent is an isoparaffin stretching agent.

13. The method of claim 1 wherein the stretching of the layer comprises stretching the layer of PTFE in the direction transverse at a rate of 15 percent per second to 25 percent per second.

14. The method of claim 1 further comprising calendering the stretched layer of PTFE to densify and compress the layer of PTFE.

15. The method of claim 1 wherein the PTFE ribbon extrudate has a ribbon configuration and a thickness of 0.020 inch to 0.040 inch.

16. The method of claim 1 wherein the PTFE ribbon extrudate is calendered in the machine direction to a reduced thickness of 0.001 inch to 0.005 inch prior to stretching.

17. The method of claim 1 further comprising sintering the stretched layer of PTFE.

18. The method of claim 17, wherein the step of sintering is at 350° C. to 380° C. from 2 to 5 minutes.

* * * * *